US012736624B2

(12) United States Patent
Karnam et al.

(10) Patent No.: US 12,736,624 B2
(45) Date of Patent: Sep. 15, 2026

(54) RADAR-BASED MOVEMENT SENSORS ARRANGED IN A DOMESTIC SETTING

(71) Applicant: Plume Design, Inc., Palo Alto, CA (US)

(72) Inventors: Raghavender Rao Karnam, Milpitas, CA (US); Konstantinos Antonios Dimitriou, San Francisco, CA (US)

(73) Assignee: PLUME DESIGN, INC., Palo Alto, CA (US)

( * ) Notice: Subject to any disclaimer, the term of this patent is extended or adjusted under 35 U.S.C. 154(b) by 275 days.

(21) Appl. No.: 17/693,805

(22) Filed: Mar. 14, 2022

(65) Prior Publication Data

US 2023/0288536 A1 Sep. 14, 2023

(51) Int. Cl.

| | |
|---|---|
| ***G01S 7/41*** | (2006.01) |
| ***A61B 5/00*** | (2006.01) |
| ***A61B 5/11*** | (2006.01) |
| ***G01S 13/50*** | (2006.01) |
| ***G01S 13/56*** | (2006.01) |
| ***G01S 13/89*** | (2006.01) |

(52) U.S. Cl.

CPC ............ *G01S 7/415* (2013.01); *A61B 5/1117* (2013.01); *A61B 5/4809* (2013.01); *G01S 13/505* (2013.01); *G01S 13/56* (2013.01); *G01S 13/89* (2013.01)

(58) Field of Classification Search

CPC ........ G01S 7/415; G01S 13/505; G01S 13/56; G01S 13/89; A61B 5/1117; A61B 5/4809

See application file for complete search history.

(56) References Cited

U.S. PATENT DOCUMENTS

| | | | | |
|---|---|---|---|---|
| 2016/0041617 | A1* | 2/2016 | Poupyrev | G01S 13/04 345/156 |
| 2017/0329449 | A1* | 11/2017 | Silverstein | G01S 13/56 |
| 2020/0204541 | A1* | 6/2020 | Nair | H04L 63/0853 |
| 2020/0233079 | A1* | 7/2020 | Silverstein | G08B 21/18 |
| 2021/0318427 | A1* | 10/2021 | Wang | G01S 13/505 |
| 2022/0252712 | A1* | 8/2022 | Song | G01S 13/58 |
| 2023/0018686 | A1* | 1/2023 | Shin | G01S 7/35 |
| 2023/0253103 | A1* | 8/2023 | Dos Santos | A63B 71/0622 |
| 2023/0341518 | A1* | 10/2023 | Rajab | A61B 5/1118 |

* cited by examiner

*Primary Examiner* — Nazra Nur Waheed

(74) *Attorney, Agent, or Firm* — Nicholas Martin; Greenberg Traurig, LLP

(57) ABSTRACT

Systems and methods for using radar-based detection in a home environment and utilizing this detection for identifying human behavior are provided. A system, according to one implementation, includes a processing device and a memory device configured to store instructions that, when executed, enable the processing device to obtain movement data from one or more radar-based sensing devices arranged within a predefined setting. The instructions further enable the processing device to analyze the movement data to identify a human activity and to determine one or more characteristics of the human activity. Also, the processing device is configured to analyze the human activity and the one or more characteristics of the human activity to determine an identity of a person performing the human activity.

29 Claims, 10 Drawing Sheets

$f_{out}$ $f_{in}=f_{out}+f_{Doppler}$

CW
(velocity only)

t=2r/c

Pulsed
(range only)

$T_p$ $t_{diff}=T_p-2v_rT_p$

Pulsed-Doppler
(range and velocity)

$f_{out}(t)$ $f_{in}(t)=f_{out}(t)+f_{Doppler}$

FMCW
(velocity and range)

520

522

570

600

610

RADAR-BASED MOVEMENT SENSORS ARRANGED IN A DOMESTIC SETTING

FIELD OF THE DISCLOSURE

The present disclosure generally relates to Wi-Fi systems. More particularly, the present disclosure relates to utilizing radar-based sensors incorporated in one or more access points of a local Wi-Fi network, such as for detecting movement activities in a domestic setting.

BACKGROUND OF THE DISCLOSURE

Generally, life expectancy in developed countries continues to rise. As a result, population statistics show an increase in the percentage of senior citizens (e.g., people above about 65 years of age) among the entire population. Thus, research into aging, age-related conditions, etc. has been conducted to support an aging population. For example, the concept of Ambient Assisted Living (AAL) can be defined as "the use of information and communication technologies (ICT) in a person's daily living and working environment to enable them to stay active longer, remain socially connected and live independently into old age" (www.aal-europe.eu). Also, the Center for Disease Control and Prevention (CDC) defines the concept of "aging in place" as "the ability to live in one's own home and community safely, independently, and comfortably, regardless of age, income, or ability level." Research in the field of aging at home includes understanding normal human behavior and monitoring human activity in a domestic environment. More particularly, event detection (e.g., fall detection) is a specific area of concern in aging in place and AAL research.

In many cases, event detection typically requires a person (who is being monitored) to wear a sensor or electronic device (e.g., on his or her wrist, waist, or ankle) or to carry a sensor or electronic device (e.g., a cell phone, etc.) in his or her hand or pocket. However, these devices are not worn or carried at all times. For instance, a person might typically remove a wearable device (or put down a cell phone) while using a bathroom, where many fall events often occur. Since these types of devices would therefore not be able to detect fall events in these cases, technology may include image-based or vision-based detectors, which may be used throughout a home for detecting falls or other events. However, an obvious shortcoming in this regard is that vision-based sensors are often considered to be an invasion of privacy, especially in a bathroom setting.

Therefore, there is a need in the field of "aging in place" and AAL to provide "non-intrusive" sensors arranged in a home for sensing human activities (e.g., walking, falling, etc.) and analyzing characteristics of these human activities, particular to determine when a specific response (e.g., automatic notification to emergency personnel) is needed. There is also a need for allowing individuals to live independently (e.g., in their own homes) while also enabling the non-invasive detection of human activities in smart home environments.

BRIEF SUMMARY OF THE DISCLOSURE

The present disclosure relates to systems and methods that may be incorporated in smart home systems, particularly for allowing an eldering person to age in place or age at home with independence and without intrusive detection. One implementation of a system includes a processing device and a memory device configured to store instructions. For instructions, for example, are configured to enable the processing device to obtain movement data from one or more radar-based sensing devices arranged within a predefined setting. The instructions also enable the processing device to analyze the movement data to identify a human activity and to determine one or more characteristics of the human activity. Also, the instructions allow the processing device to analyze the human activity and the one or more characteristics of the human activity to determine an identity of a person performing the human activity.

For example, each of the one or more radar-based sensing devices may be housed in an access point of a local Wi-Fi network. The movement data may include micro-Doppler data based on reflection signals received by the one or more radar-based sensing devices with respect to time. The one or more radar-based sensing devices may be configured to utilize one or more of Intermediate Frequency (IF) signals, Frequency Modulation (FM) signals, Continuous Wave (CW) signals, Frequency Modulation Continuous Wave (FMCW) signals, Ultra-Wideband (UWB) signals, in-phase signals, quadrature signals, pulsed reflection signals, pulsed Doppler signals, micro-Doppler signals, distance-indicating signals, and time-series signals.

The predefined setting may be a domestic environment having a plurality of spaces or rooms, where a plurality of radar-based sensing devices may be oriented at one or more angles and configured to monitor one or more of the spaces or rooms of the domestic environment. The human activity, for example, may be identified out of a plurality of detectable actions, such as walking, running, falling, rising from a seated or lying position, lowering into a seated or lying position, exercising, carrying objects, cooking, cleaning, using a home appliance, using a computer or mobile device, opening or closing a door, moving in a wheelchair or scooter, or walking with the assistance of a walker or cane. In some examples, the one or more characteristics of the human activity may be identified out of a plurality of detectable parameters including speed, acceleration, direction, location within the predefined setting, gait, balance, steadiness, variability, physical well-being, and/or behavioral well-being.

The instructions may further enable the processing device to characterize the human activity in a spectrogram and then utilize the spectrogram to determine the one or more characteristics of the human activity. The step of determining the identity of the person performing the human activity may include distinguishing the identity of the person from one or more other people in the predefined setting. The step of distinguishing the identity of the person from the one or more other people may include clustering the movement data based at least on location information to identify a plurality of people in the predefined setting. The step of determining the identity of the person performing the human activity may include comparing the one or more characteristics of the human activity with pre-stored behavioral patterns. For example, the pre-stored behavioral patterns may be based on a) supervised training data obtained by monitoring the person and used for training a Machine Learning (ML) model and/or b) generalized data representing normal human behavior obtained by monitoring a test subject in a lab.

The instructions may further enable the processing device to obtain audio data from the predefined setting when the movement data is obtained. Then, the processing device may combine the audio data with the movement data to enhance the identifying of the human activity and the detection of the one or more characteristics of the human activity. The processing device may be further configured to compare the one or more characteristics of the human activity with pre-stored normal human behavior or with historic data associated with the identified person. Then, a health or safety risk can be determined based on the comparison. Also, an automatic notification can be provided (e.g., to a caregiver) if the health or safety risk is greater than a predetermined threshold.

The step of analyzing the movement data to identify the human activity may include identifying non-human motion data and filtering out the non-human motion data from the movement data. Identifying the non-human motion data, for example, may include identifying one or more actions performed by a pet, a robot vacuum device, a door, a drawer, a fan, and a home appliance.

Also, the systems and methods may include automatically performing one or more responsive actions based on a) the identification of the human activity, b) the one or more characteristics of the human activity, and/or c) the identity of the person performing the human activity. For instance, the one or more responsive actions may include controlling lights, controlling an HVAC system, controlling a security system, controlling utility appliances, controlling kitchen appliances, controlling entertainment devices, and/or sending an alert to a family member or a medical or emergency professional.

Before monitoring the movement data, the processing device may be configured to perform pre-processing actions on the movement data. The pre-processing actions, for example, may include one or more of normalization, clipping, band pass filtering, DC offset removal, noise reduction, and grouping samples of the movement data to balance resolution in the time and frequency domains. In addition, the processing device may be configured to monitor an identity and location of a wireless device associated with the person to enhance determining the identity of the person performing the human activity. The wireless device may be a mobile phone, a wearable electronic device, an Ultra-Wideband (UWB) tracker tag, etc.

BRIEF DESCRIPTION OF THE DRAWINGS

The present disclosure is illustrated and described herein with reference to the various drawings, in which like reference numbers are used to denote like system components/method steps, as appropriate, and in which.

DETAILED DESCRIPTION OF THE DISCLOSURE

The present disclosure relates to systems and methods for utilizing non-intrusive sensors in a domestic environment for sensing human movement. The data obtained from the sensed human movement can be analyzed to determine what type of human movement is being performed or what activity is being performed. For example, some detectable actions or activities may include walking, running, rising from a seated position, doing laundry, carrying groceries, cooking, etc. Also, once the specific activity is determined, the data may also be analyzed to determine certain qualities or characteristics of the activity. For example, some characteristics of walking may include speed, direction, stability, limping patterns, etc. Also, the processed data can be further analyzed to associate the identified human activity (and quality thereof) to a particular person. If multiple people are in a space, the systems and methods can distinguish one person from another, which may be based on known or historic data obtained for each person over time.

Distributed Wi-Fi System

Figure 1:
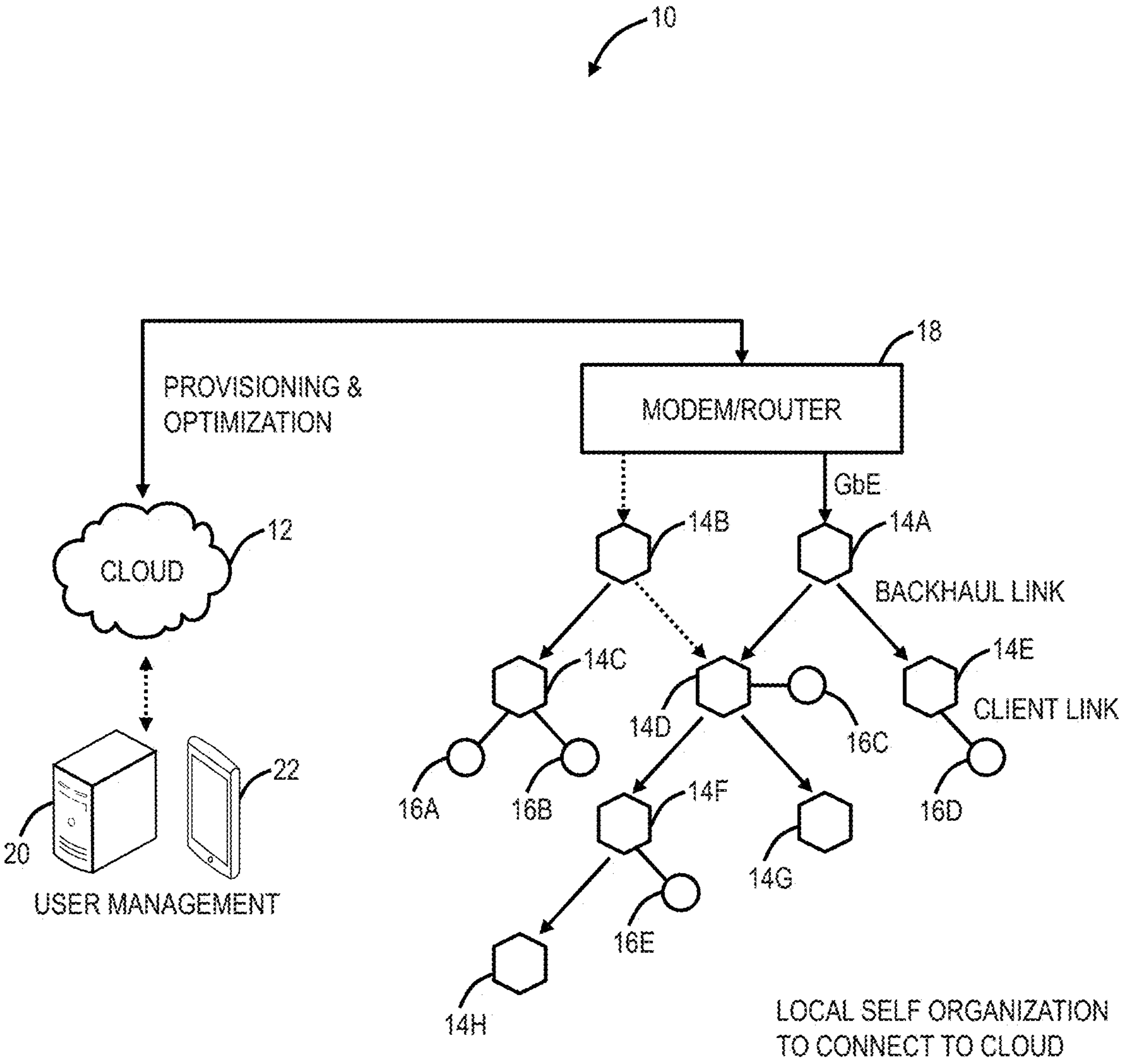
FIG. 1 is a network diagram of a distributed Wi-Fi system with cloud-based control and management, according to various embodiments.

FIG. 1 is a network diagram of a distributed Wi-Fi system 10 with control via a cloud 12 service. The distributed Wi-Fi system 10 can operate in accordance with the IEEE 802.11 protocols and variations thereof. The distributed Wi-Fi system 10 includes a plurality of access points 14 (labeled as access points 14A-14H), which can be distributed throughout a location, such as a residence, office, or the like. That is, the distributed Wi-Fi system 10 contemplates operation in any physical location where it is inefficient or impractical to service with a single access point, repeaters, or a mesh system. As described herein, the distributed Wi-Fi system 10 can be referred to as a network, a system, a Wi-Fi network, a Wi-Fi system, a cloud-based system, etc. The access points 14 can be referred to as nodes, access points, Wi-Fi nodes, Wi-Fi access points, etc. The objective of the access points 14 is to provide network connectivity to Wi-Fi client devices 16 (labeled as Wi-Fi client devices 16A-16E). The Wi-Fi client devices 16 can be referred to as client devices, user devices, clients, Wi-Fi clients, Wi-Fi devices, etc.

In a typical residential deployment, the distributed Wi-Fi system 10 can include from about 3 to about 12 access points or more in a home. A large number of access points 14

(which can also be referred to as nodes in the distributed Wi-Fi system 10) ensures that the distance between any access point 14 is always small, as is the distance to any Wi-Fi client device 16 needing Wi-Fi service. That is, an objective of the distributed Wi-Fi system 10 can be for distances between the access points 14 to be of comparable size as distances between the Wi-Fi client devices 16 and the associated access point 14. Such small distances ensure that every corner of a consumer's home is well covered by Wi-Fi signals. It also ensures that any given hop in the distributed Wi-Fi system 10 is short and goes through few walls. This results in strong signal strengths for each hop in the distributed Wi-Fi system 10, allowing the use of high data rates, and providing robust operation. Note, those skilled in the art will recognize the Wi-Fi client devices 16 can be mobile devices, tablets, computers, consumer electronics, home entertainment devices, televisions, IoT devices, or any network-enabled device. For external network connectivity, one or more of the access points 14 can be connected to a modem/router 18, which can be a cable modem, Digital Subscriber Loop (DSL) modem, or any device providing external network connectivity to the physical location associated with the distributed Wi-Fi system 10.

While providing excellent coverage, a large number of access points 14 (nodes) presents a coordination problem. Getting all the access points 14 configured correctly and communicating efficiently requires centralized control. This cloud 12 service can provide control via servers 20 that can be reached across the Internet and accessed remotely, such as through an application ("app") running on a user device 22. The running of the distributed Wi-Fi system 10, therefore, becomes what is commonly known as a "cloud service." The servers 20 are configured to receive measurement data, to analyze the measurement data, and to configure the access points 14 in the distributed Wi-Fi system 10 based thereon, through the cloud 12. The servers 20 can also be configured to determine which access point 14 each of the Wi-Fi client devices 16 connects (associates) with. That is, in an example aspect, the distributed Wi-Fi system 10 includes cloud-based control (with a cloud-based controller or cloud service in the cloud) to optimize, configure, and monitor the operation of the access points 14 and the Wi-Fi client devices 16. This cloud-based control is contrasted with a conventional operation that relies on a local configuration, such as by logging in locally to an access point. In the distributed Wi-Fi system 10, the control and optimization does not require local login to the access point 14, but rather the user device 22 (or a local Wi-Fi client device 16) communicating with the servers 20 in the cloud 12, such as via a disparate network (a different network than the distributed Wi-Fi system 10) (e.g., LTE, another Wi-Fi network, etc.).

The access points 14 can include both wireless links and wired links for connectivity. In the example of FIG. 1, the access point 14A has an example gigabit Ethernet (GbE) wired connection to the modem/router 18. Optionally, the access point 14B also has a wired connection to the modem/router 18, such as for redundancy or load balancing. Also, the access points 14A, 14B can have a wireless connection to the modem/router 18. The access points 14 can have wireless links for client connectivity (referred to as a client link) and for backhaul (referred to as a backhaul link). The distributed Wi-Fi system 10 differs from a conventional Wi-Fi mesh network in that the client links and the backhaul links do not necessarily share the same Wi-Fi channel, thereby reducing interference. That is, the access points 14 can support at least two Wi-Fi wireless channels—which can be used flexibly to serve either the client link or the backhaul link and may have at least one wired port for connectivity to the modem/router 18, or for connection to other devices. In the distributed Wi-Fi system 10, only a small subset of the access points 14 require direct connectivity to the modem/router 18 with the non-connected access points 14 communicating with the modem/router 18 through the backhaul links back to the connected access points 14.

Distributed Wi-Fi System Compared to Other Wi-Fi Systems

Figure 2:
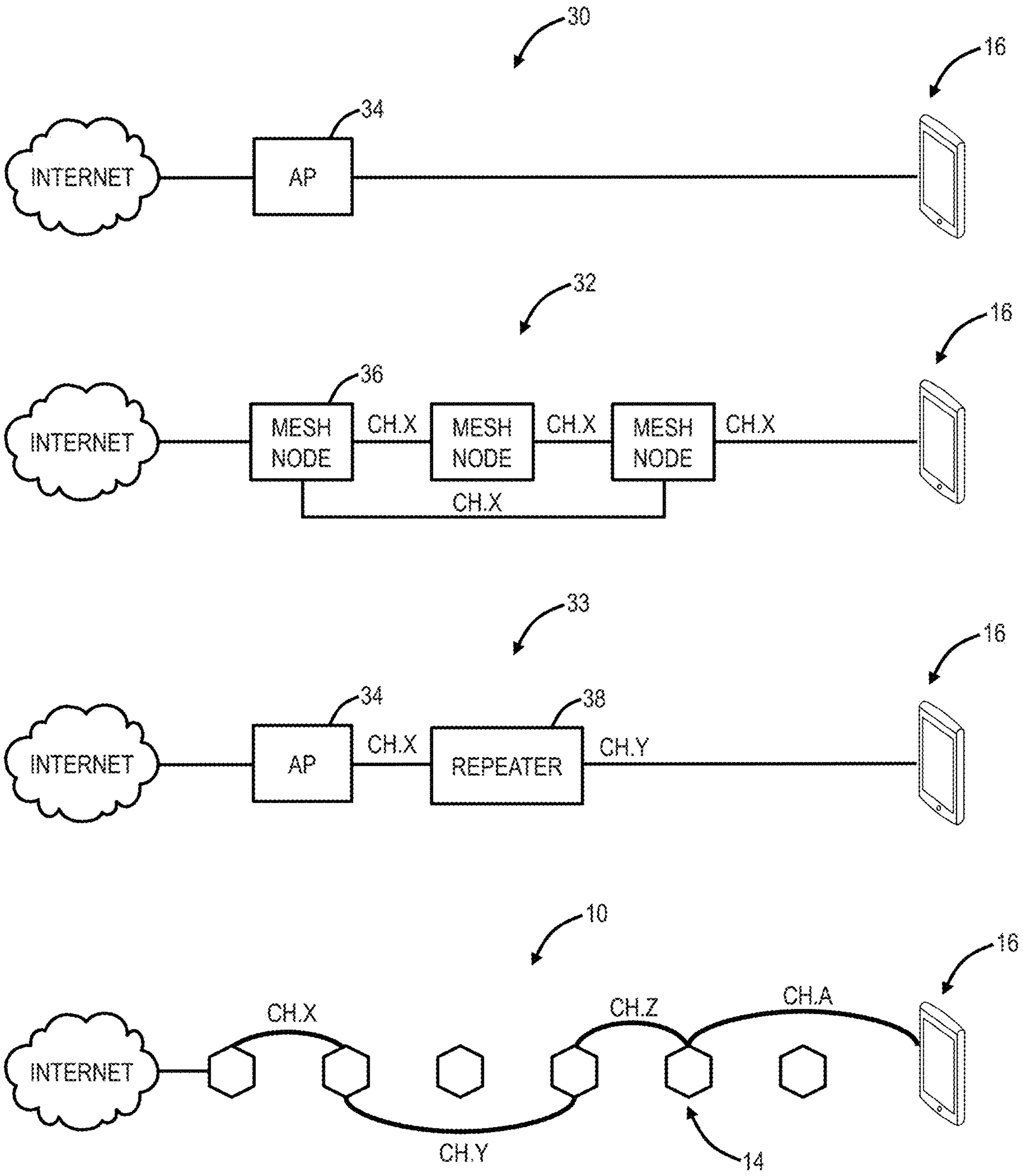
FIG. 2 is a network diagram illustrating the differences in the operation of the distributed Wi-Fi system of FIG. 1 relative to a conventional single access point system, a Wi-Fi mesh network, and a Wi-Fi repeater network, according to various embodiments.

FIG. 2 is a network diagram illustrating the differences in the operation of the distributed Wi-Fi system 10 of FIG. 1 relative to a conventional single access point system 30 (first system), a Wi-Fi mesh network 32 (second system), and a Wi-Fi repeater network 33 (third system). The first three systems can be compared with the fourth system (e.g., the distributed Wi-Fi system 10) of the preferred embodiment.

As shown in the first system, the single access point system 30 relies on a single, high-powered access point 34, which may be centrally located to serve all Wi-Fi client devices 16 in a location (e.g., house). Again, as described herein, in a typical residence, the single access point system 30 can have several walls, floors, etc. between the access point 34 and the Wi-Fi client devices 16. Plus, the single access point system 30 operates on a single channel, leading to potential interference from neighboring systems.

As shown in the second system, the Wi-Fi mesh network 32 solves some of the issues with the single access point system 30 by having multiple mesh nodes 36, which distribute the Wi-Fi coverage. Specifically, the Wi-Fi mesh network 32 operates based on the mesh nodes 36 being fully interconnected with one another, sharing a channel such as a channel X between each of the mesh nodes 36 and the Wi-Fi client device 16. That is, the Wi-Fi mesh network 32 is a fully interconnected grid, sharing the same channel, and allowing multiple different paths between the mesh nodes 36 and the Wi-Fi client device 16. However, since the Wi-Fi mesh network 32 uses the same backhaul channel, every hop between source points divides the network capacity by the number of hops taken to deliver the data. For example, if it takes three hops to stream a video to a Wi-Fi client device 16, the Wi-Fi mesh network 32 is left with only ⅓ the capacity.

As shown in the third system, the Wi-Fi repeater network 33 includes the access point 34 coupled wirelessly to a Wi-Fi repeater 38. The Wi-Fi repeater network 33 is a star topology where there is at most one Wi-Fi repeater 38 between the access point 14 and the Wi-Fi client device 16. From a channel perspective, the access point 34 can communicate to the Wi-Fi repeater 38 on a first channel, Ch. X, and the Wi-Fi repeater 38 can communicate to the Wi-Fi client device 16 on a second channel, Ch. Y.

As shown in the fourth system (e.g., the distributed Wi-Fi system 10), this configuration solves the problem with the Wi-Fi mesh network 32 of requiring the same channel for all connections by using a different channel or band for the various hops (note, some hops may use the same channel/band, but it is not required), to prevent slowing down the Wi-Fi speed. For example, the distributed Wi-Fi system 10 can use different channels/bands between access points 14 and between the Wi-Fi client device 16 (e.g., Chs. X, Y, Z, A), and also, the distributed Wi-Fi system 10 does not necessarily use every access point 14, based on configuration and optimization by the cloud 12. The distributed Wi-Fi system 10 solves the problems of the single access point system 30 by providing multiple access points 14. The distributed Wi-Fi system 10 is not constrained to a star topology as in the Wi-Fi repeater network 33, which at most allows two wireless hops between the Wi-Fi client device 16 and a gateway. Also, the distributed Wi-Fi system 10 forms a tree topology where there is one path between the Wi-Fi client device 16 and the gateway, but which allows for multiple wireless hops, unlike the Wi-Fi repeater network 33.

Wi-Fi is a shared, simplex protocol meaning only one conversation between two devices can occur in the network at any given time, and if one device is talking the others need to be listening. By using different Wi-Fi channels, multiple simultaneous conversations can happen simultaneously in the distributed Wi-Fi system 10. By selecting different Wi-Fi channels between the access points 14, interference and congestion are avoided. The server 20 through the cloud 12 automatically configures the access points 14 in an optimized channel hop solution. The distributed Wi-Fi system 10 can choose routes and channels to support the ever-changing needs of consumers and their Wi-Fi client devices 16. The distributed Wi-Fi system 10 approach is to ensure Wi-Fi signals do not need to travel far—either for backhaul or client connectivity. Accordingly, the Wi-Fi signals remain strong and avoid interference by communicating on the same channel as in the Wi-Fi mesh network 32 or with Wi-Fi repeaters. In an example aspect, the servers 20 in the cloud 12 are configured to optimize channel selection for the best user experience.

Of note, the present disclosure for intelligent monitoring is not limited to the distributed Wi-Fi system 10 but contemplates any of the Wi-Fi networks 10, 30, 32, 33, with monitoring through the cloud 12. For example, different vendors can make access points 14, 34, mesh nodes 36, repeaters 38, etc. However, it is possible for unified control via the cloud using standardized techniques for communication with the cloud 12. One such example includes OpenSync, sponsored by the Applicant of the present disclosure and described at www.opensync.io/documentation. OpenSync is cloud-agnostic open-source software for the delivery, curation, and management of services for the modern home. That is, this provides standardization of the communication between devices and the cloud 12. OpenSync acts as silicon, Customer Premises Equipment (CPE), and cloud-agnostic connection between the in-home hardware devices and the cloud 12. This is used to collect measurements and statistics from the connected Wi-Fi client devices 16 and network management elements, and to enable customized connectivity services.

Cloud-Based Wi-Fi Management

Conventional Wi-Fi systems utilize local management, such as where a user on the Wi-Fi network connects to a designated address (e.g., 192.168.1.1, etc.). The distributed Wi-Fi system 10 is configured for cloud-based management via the servers 20 in the cloud 12. Also, the single access point system 30, the Wi-Fi mesh network 32, and the Wi-Fi repeater network 33 can support cloud-based management as described above. For example, the APs 34 and/or the mesh nodes 36 can be configured to communicate with the servers 20 in the cloud 12. This configuration can be through a software agent installed in each device or the like, e.g., OpenSync. As described herein, cloud-based management includes reporting of Wi-Fi related performance metrics to the cloud 12 as well as receiving Wi-Fi-related configuration parameters from the cloud 12. The systems and methods contemplate use with any Wi-Fi system (i.e., the distributed Wi-Fi system 10, the single access point system 30, the Wi-Fi mesh network 32, and the Wi-Fi repeater network 33, etc.), including systems that only support reporting of Wi-Fi related performance metrics (and not supporting cloud-based configuration).

The cloud 12 utilizes cloud computing systems and methods abstract away physical servers, storage, networking, etc. and instead offer these as on-demand and elastic resources. The National Institute of Standards and Technology (NIST) provides a concise and specific definition which states cloud computing is a model for enabling convenient, on-demand network access to a shared pool of configurable computing resources (e.g., networks, servers, storage, applications, and services) that can be rapidly provisioned and released with minimal management effort or service provider interaction. Cloud computing differs from the classic client-server model by providing applications from a server that are executed and managed by a client's web browser or the like, with no installed client version of an application required. Centralization gives cloud service providers complete control over the versions of the browser-based and other applications provided to clients, which removes the need for version upgrades or license management on individual client computing devices. The phrase SaaS is sometimes used to describe application programs offered through cloud computing. A common shorthand for a provided cloud computing service (or even an aggregation of all existing cloud services) is "the cloud."

Local Wi-Fi Network

Figure 3:
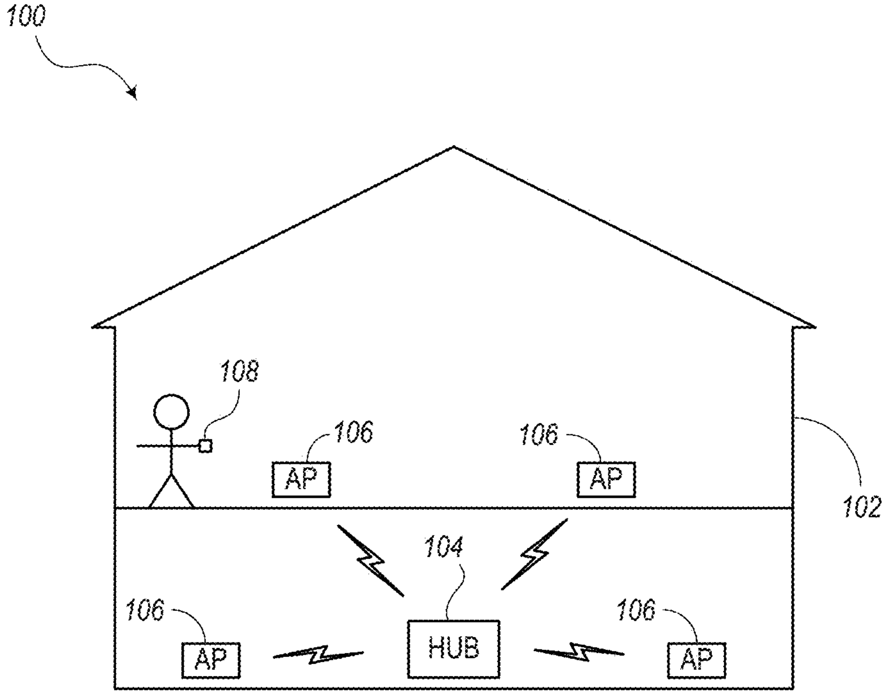
FIG. 3 is a diagram illustrating a local Wi-Fi network of the distributed Wi-Fi system of FIG. 1, according to various embodiments.

FIG. 3 is a diagram illustrating a local Wi-Fi network 100, which may utilize the distributed Wi-Fi system 10 of FIG. 1 (and/or the fourth system shown in FIG. 2). In some embodiments, the local Wi-Fi network 100 may be arranged in a home 102, apartment, assisted living facility, office, or other suitable residential, domestic, or business settings. It may be noted that the home 102 (or other setting or environment) may include a plurality of rooms or spaces having any type of layout and covering one or more floors. The local Wi-Fi network 100 may be referred to as a "smart home" system.

According to some embodiments, the local Wi-Fi network 100 may include a hub device 104 and one or more access points 106 arranged in any suitable configuration within the home 102. Particularly, each of the access points 106, according to some embodiments, may include one or more radar-based sensors incorporated in the housing of the respective access point 106. In some embodiments, the hub device 104 and access points 106 may be substantially stationary devices and may be arranged, for instance, in the configuration shown in the fourth system of FIG. 2. The hub device 104 and access points 106 may have similar functionality except that the hub device 104 may be configured for communication over the Internet. For example, the hub device 104 may be a central access point or other centralized device for receiving sensor data from each of the access points 106 and then processing the sensor signals from multiple access points 106 throughout the home 102.

Also, according to some embodiments, the local Wi-Fi network 100 may further include one or more tracker tags 108. Each tracker tag 108 may be configured as a mobile or portable tag element having electronics that enable tracking or locating of the tracker tag 108 itself. Thus, as a mobile component, the tracker tags 108 can be worn or carried by one or more people in the home 102 and track the location of these people throughout the home 102. The tracker tags 108 can be attached to clothing, shoes, purses, key chains, etc. Location information can be combined with time (clock) information for determining certain metrics, such as how long a person spends in a particular room (e.g., bathroom, bedroom, etc.).

In some cases, the hub device 104 may also be configured with one or more sensors. It should be noted that sensors are not normally housed in access points according to conventional design. However, in the embodiments of the present disclosure, the access points 106 may be configured with sensors, specifically for detecting movement that can be used for identifying human activities (e.g., walking, falling, etc.). According to the embodiments of the present disclosure, the sensors are based on radar technology and do not utilize cameras or other more intrusive visual detection components. Therefore, with radar, the sensors are configured to sense general motion or movement characteristics within the rooms and spaces of the home 102.

The tracker tags 108 may be used for communication with the hub device 104 and/or access points 106 (or sensors). Based on communication with the tracker tags 108, it may be possible to track the location of a person associated with the tracker tag 108, such as when the person has the tracker tag 108 in his or her pocket, attached to his or her clothing, around his or her wrist, or worn or attached in any other suitable manner. Also, the location information obtained from the tracker tag 108 may be used to enhance the detection of the identity of the person performing certain human activities by comparing the location information deduced from the radar sensing information and the location information deduced from the tracking information of the tracker tag 108. The location information can also be used with time information to determine how long someone stays in a bed, stays in a bathroom, etc.

Hub Device Architecture

Figure 4:
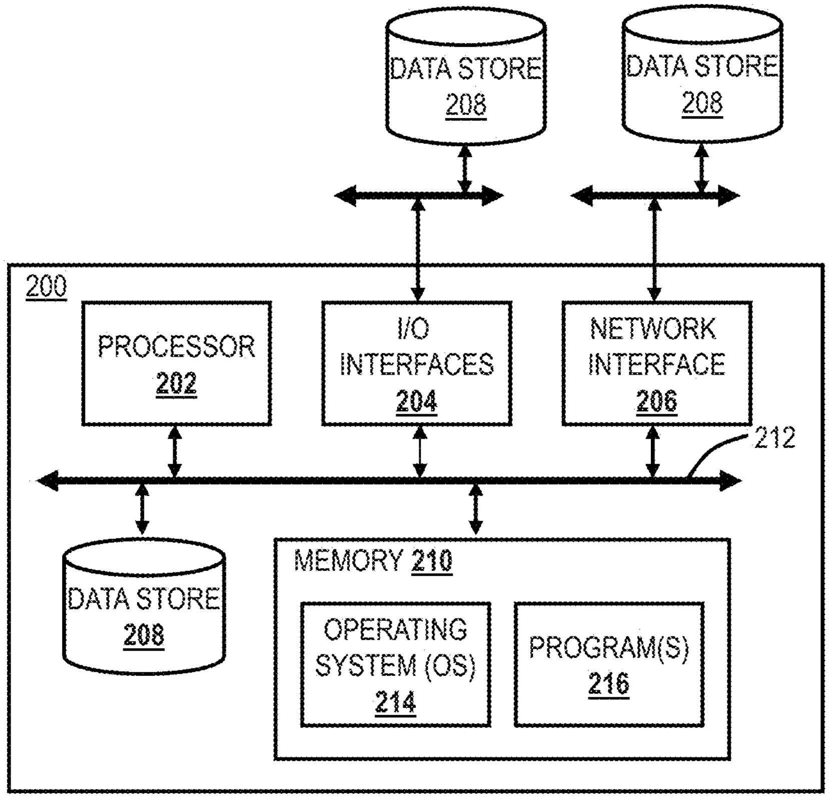
FIG. 4 is a block diagram of a hub device shown in the local Wi-Fi network of FIG. 3, according to various embodiments.

FIG. 4 is a block diagram of a hub device 200, such as the hub device 104 shown in the local Wi-Fi network 100 of FIG. 3. In some embodiments, the hub device 200 may be configured as a server which may be used in the cloud 12, in other systems, or in a standalone application. The hub device 200 may be a digital computer that, in terms of hardware architecture, generally includes a processor 202, input/output (I/O) interfaces 204, a network interface 206, a data store 208, and memory 210. It should be appreciated by those of ordinary skill in the art that FIG. 4 depicts the hub device 200 in an oversimplified manner, and a practical embodiment may include additional components and suitably configured processing logic to support known or conventional operating features that are not described in detail herein. The components (202, 204, 206, 208, and 210) are communicatively coupled via a local interface 212. The local interface 212 may be, for example, but not limited to, one or more buses or other wired or wireless connections, as is known in the art. The local interface 212 may have additional elements, which are omitted for simplicity, such as controllers, buffers (caches), drivers, repeaters, and receivers, among many others, to enable communications. Further, the local interface 212 may include address, control, and/or data connections to enable appropriate communications among the aforementioned components.

The processor 202 is a hardware device for executing software instructions. The processor 202 may be any custom made or commercially available processor, a central processing unit (CPU), an auxiliary processor among several processors associated with the hub device 200, a semiconductor-based microprocessor (in the form of a microchip or chipset), or generally any device for executing software instructions. When the hub device 200 is in operation, the processor 202 is configured to execute software stored within the memory 210, to communicate data to and from the memory 210, and to generally control operations of the hub device 200 pursuant to the software instructions. The I/O interfaces 204 may be used to receive user input from and/or for providing system output to one or more devices or components. The user input may be provided via, for example, a keyboard, touchpad, and/or a mouse. System output may be provided via a display device and a printer (not shown). I/O interfaces 204 may include, for example, a serial port, a parallel port, a small computer system interface (SCSI), a serial ATA (SATA), a fiber channel, Infiniband, iSCSI, a PCI Express interface (PCI-x), an infrared (IR) interface, a radio frequency (RF) interface, and/or a universal serial bus (USB) interface.

The network interface 206 may be used to enable the hub device 200 to communicate on a network, such as the Internet. The network interface 206 may include, for example, an Ethernet card or adapter (e.g., 10BaseT, Fast Ethernet, Gigabit Ethernet, 10 GbE) or a wireless local area network (WLAN) card or adapter (e.g., 802.11a/b/g/n/ac). The network interface 206 may include address, control, and/or data connections to enable appropriate communications on the network. A data store 208 may be used to store data. The data store 208 may include any of volatile memory elements (e.g., random access memory (RAM, such as DRAM, SRAM, SDRAM, and the like)), nonvolatile memory elements (e.g., ROM, hard drive, tape, CDROM, and the like), and combinations thereof. Moreover, the data store 208 may incorporate electronic, magnetic, optical, and/or other types of storage media. In one example, the data store 208 may be located internal to the hub device 200, such as, for example, an internal hard drive connected to the local interface 212 in the hub device 200. Additionally, in another embodiment, the data store 208 may be located external to the hub device 200 such as, for example, an external hard drive connected to the I/O interfaces 204 (e.g., SCSI or USB connection). In a further embodiment, the data store 208 may be connected to the hub device 200 through a network, such as, for example, a network-attached file server.

The memory 210 may include any of volatile memory elements (e.g., random access memory (RAM, such as DRAM, SRAM, SDRAM, etc.)), nonvolatile memory elements (e.g., ROM, hard drive, tape, CDROM, etc.), and combinations thereof. Moreover, the memory 210 may incorporate electronic, magnetic, optical, and/or other types of storage media. Note that the memory 210 may have a distributed architecture, where various components are situated remotely from one another but can be accessed by the processor 202. The software in memory 210 may include one or more software programs, each of which includes an ordered listing of executable instructions for implementing logical functions. The software in the memory 210 includes a suitable operating system (O/S) 214 and one or more programs 216. The operating system 214 essentially controls the execution of other computer programs, such as the one or more programs 216, and provides scheduling, input-output control, file and data management, memory management, and communication control and related services. The one or more programs 216 may be configured to implement the various processes, algorithms, methods, techniques, etc. described herein.

In some embodiments, the hub device 200 may further include a Wi-Fi communication device for enabling Wi-Fi communication with the one or more access points 106. In this way, the hub device 200 can receive sensor data from the access points 106 as a result of the radar-based sensing performed at each of the access points 106. Then, the processor 202, executing instructions of the programs 216, may be configured to analyze the sensor data to identify human activities (e.g., walking, falling, etc.) and further analyze the data to detect certain qualities of the human activities (e.g., speed, stability, etc.). Also, the programs 216 may allow the processor 202 to identify one or more people in the home 102 based on behavioral patterns and historic data stored in the memory 210 or data store 208 regarding each person.

The data store 208 may be configured to store in-house (domestic) data from a number of people monitored in the home 102. The data store 208 may record person profiles for each of a number of people. In some cases, if a visitor enters the home 102 and is monitored, the user may decide to utilize the smart home system to remove information about this visitor if there is not a need to store this information. Also, data regarding caregivers may be stored in the data store 208. The data store 208 may also be configured to store trends in the data which may be analyzed by the processor 202. The processor 202 can also determine certain daily or weekly rituals or habits from the human activities and store information about the daily or weekly behaviors in the data store 208.

Also, in some embodiments, the hub device 200 may include sensors (e.g., radar-based movement sensing devices, microphones, or other audio sensing devices, and/or other sensing devices). In this way, the hub device 200 may also sense human activities in the room or space where the hub device 200 is located. The obtained information can be combined with the data from the other access points 106 or other similar radar-based sensing devices.

Then, from the accumulated data, the movement information can be analyzed to determine the type of human activity being monitored and specific characteristics or parameters of these activities (e.g., speed and direction of movement). Also, the hub device 200 may be configured to further analyze the information to determine who is performing the specific actions and correlate this information with known movement patterns of the person. In some embodiments, the hub device 200 may use machine learning to train a model that can be used to characteristic the movement for each of a number of people moving about in the home 102.

Sensor Architecture

Figure 5:
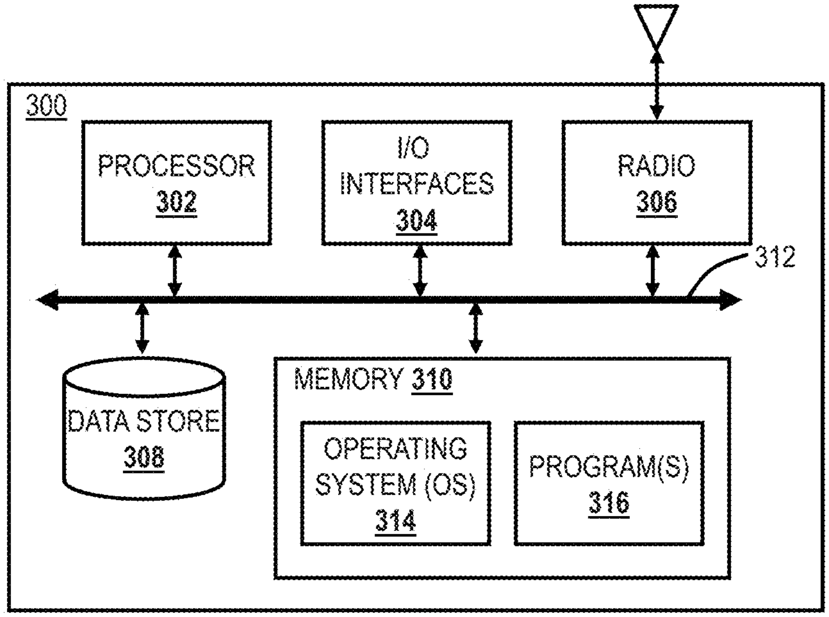
FIG. 5 is a block diagram of one of the access points shown in the local Wi-Fi network of FIG. 3, according to various embodiments.

FIG. 5 is a block diagram of a sensor 300 (e.g., one of the access points 106 shown in the local Wi-Fi network 100 of FIG. 3). In this embodiment, the sensor 300 (or some or all of the sensors) may be arranged or incorporated in an access point 106 and may transmit sensor signals to the hub device 200 for processing. In other embodiments, the sensor 300 may be arranged in its own housing and may communicate with a nearby access point for send sensor information to a central or hub device (e.g., hub device 200) for processing the sensor data. With multiple sensors 300 distributed throughout an environment (e.g., home 102), many (or essentially all) of the spaces within the home 102 can be monitored to detect human activities. The sensor 300 operates using radar and normally would not include image detection or other more intrusive mechanisms, although visual detection may be included in some embodiments. The radar transmission and reception signals may utilize 24 GHz, 60 GHz, or other suitable frequency signals. The sensor 300, according to preferred embodiments, may be able to sense human activities without invading on the privacy of the individuals in the specific (e.g., domestic) environment.

The sensor 300 can be a digital device that, in terms of hardware architecture, generally includes a processor 302, input/output (I/O) interfaces 304, a radio 306, a data store 308, and memory 310. It should be appreciated by those of ordinary skill in the art that FIG. 4 depicts the sensor 300 in an oversimplified manner, and a practical embodiment may include additional components and suitably configured processing logic to support known or conventional operating features that are not described in detail herein. The components (302, 304, 306, 308, and 302) are communicatively coupled via a local interface 312. The local interface 312 can be, for example, but not limited to, one or more buses or other wired or wireless connections, as is known in the art. The local interface 312 can have additional elements, which are omitted for simplicity, such as controllers, buffers (caches), drivers, repeaters, and receivers, among many others, to enable communications. Further, the local interface 312 may include address, control, and/or data connections to enable appropriate communications among the aforementioned components.

The processor 302 is a hardware device for executing software instructions. The processor 302 can be any custom made or commercially available processor, a central processing unit (CPU), an auxiliary processor among several processors associated with the sensor 300, a semiconductor-based microprocessor (in the form of a microchip or chipset), or generally any device for executing software instructions. When the sensor 300 is in operation, the processor 302 is configured to execute software stored within the memory 310, to communicate data to and from the memory 310, and to generally control operations of the sensor 300 pursuant to the software instructions. In an embodiment, the processor 302 may include a mobile optimized processor such as optimized for power consumption and mobile applications. The I/O interfaces 304 (which may be omitted in some embodiments) can be used to receive user input from and/or for providing system output. User input can be provided via, for example, a keypad, a touch screen, a scroll ball, a scroll bar, buttons, a barcode scanner, and the like. System output can be provided via a display device such as a liquid crystal display (LCD), touch screen, and the like. The I/O interfaces 304 can also include, for example, a serial port, a parallel port, a small computer system interface (SCSI), an infrared (IR) interface, a radio frequency (RF) interface, a universal serial bus (USB) interface, and the like. The I/O interfaces 304 can include a graphical user interface (GUI) that enables a user to interact with the sensor 300. Additionally, the I/O interfaces 304 may further include an imaging device, i.e., camera, video camera, etc.

The radio 306 enables wireless communication to an external access device or network. Any number of suitable wireless data communication protocols, techniques, or methodologies can be supported by the radio 306, including, without limitation: RF; IrDA (infrared); Bluetooth; ZigBee (and other variants of the IEEE 802.15 protocol); IEEE 802.11 (any variation); IEEE 802.16 (WiMAX or any other variation); Direct Sequence Spread Spectrum; Frequency Hopping Spread Spectrum; Long Term Evolution (LTE); cellular/wireless/cordless telecommunication protocols (e.g., 3G/4G/5G, etc.); wireless home network communication protocols; proprietary wireless data communication protocols such as variants of Wireless USB; and any other protocols for wireless communication. The data store 308 may be used to store data. The data store 308 may include any of volatile memory elements (e.g., random access memory (RAM, such as DRAM, SRAM, SDRAM, and the like)), nonvolatile memory elements (e.g., ROM, hard drive, tape, CDROM, and the like), and combinations thereof. Moreover, the data store 308 may incorporate electronic, magnetic, optical, and/or other types of storage media.

The memory 310 may include any of volatile memory elements (e.g., random access memory (RAM, such as DRAM, SRAM, SDRAM, etc.)), nonvolatile memory elements (e.g., ROM, hard drive, etc.), and combinations thereof. Moreover, the memory 310 may incorporate electronic, magnetic, optical, and/or other types of storage media. Note that the memory 310 may have a distributed architecture, where various components are situated remotely from one another but can be accessed by the processor 302. The software in memory 310 can include one or more software programs, each of which includes an ordered listing of executable instructions for implementing logical functions. In the example of FIG. 3, the software in the memory 310 includes a suitable operating system (O/S) 314 and programs 316. The operating system 314 essentially controls the execution of other computer programs and provides scheduling, input-output control, file and data management, memory management, and communication control and related services. The programs 316 may include various applications, add-ons, etc. configured to provide end-user functionality with the sensor 300. For example, example programs 316 may include, but not limited to, a web browser, social networking applications, streaming media applications, games, mapping and location applications, electronic mail applications, financial applications, and the like. In a typical example, the end user typically uses one or more of the programs 316 along with a network.

The radio 306 may include communications circuitry and one or more antennas for enabling radar transmission and radar reception. In some embodiments, the radio 306 may be configured for Wi-Fi communication with the hub device 200 and another device may be used for radar transmission and reception. In some embodiments, the sensor 300 may also include one or more audio sensing mechanisms (e.g., microphones or the like) for obtain audio signals. By also obtaining audio signals, the hub device 200 may be configured to process these audio signals along with the movement data to enhance the detection of human activities. For example, an intense movement event followed by the sound of a door slamming could be interpreted as just a door slamming and not a person moving quickly in one direction and then stopping.

In some embodiments, the sensor 300 may include a simplified architecture for simply obtaining radar-based sensing information and transmitting this information to the hub device 200. As such, the I/O interfaces 304 may not be needed and could be omitted from the design. Also, in some cases, the data store 308 may be omitted if the movement data (and corresponding results of analyzing the movement data) from each of the sensors 300 is stored in the data store 208 of the hub device 200.

UWB Tag

Figure 6:
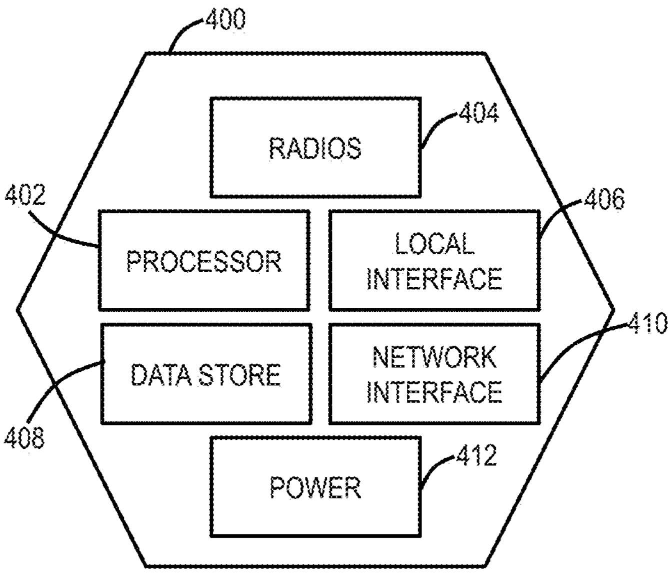
FIG. 6 is a block diagram of one of the wearable UWB tracker tags shown in the local Wi-Fi network of FIG. 3, according to various embodiments.

FIG. 6 is a block diagram of a tracker tag 400 (e.g., one of the tracker tags 108 shown in FIG. 3). In some embodiments, the tracker tag 400 may be a medical device configured to monitor physical characteristics or vital statistics of the wearer (e.g., blood pressure, heart rate, etc.) and may communicate this information to the access points 106, hub device 200, or sensors 300. In some embodiments, the tracker tag 400 may also be referred to as a wearable or portable UWB tag. The tracker tag 400 may have the form of or be incorporated in a ring, watch, jewelry, or other wearable component. In some embodiments, FIG. 6 may also represent the access points 14, 34, 36, 38 described above. The tracker tag 400 may include any suitable physical form factor and may include a processor 402, a plurality of radios 404, a local interface 406, a data store 408, a network interface 410, and power 412. It should be appreciated by those of ordinary skill in the art that FIG. 6 depicts the tracker tag 400 in an oversimplified manner, and a practical embodiment may include additional components and suitably configured processing logic to support features described herein or known or conventional operating features that are not described in detail herein.

In an exemplary embodiment, the tracker tag 400 is a compact physical implementation and may be configured to directly plug into an electrical socket and may be physically supported by the electrical plug connected to the electrical socket. This compact physical implementation can be used for a large number of access points 14, 34, 36, 38 distributed throughout a residence. The processor 402 is a hardware device for executing software instructions. The processor 402 can be any custom made or commercially available processor, a central processing unit (CPU), an auxiliary processor among several processors associated with the mobile device 300, a semiconductor-based microprocessor (in the form of a microchip or chip set), or generally any device for executing software instructions. When the access point 14, 34, 36, 38 is in operation, the processor 402 is configured to execute software stored within memory or the data store 408, to communicate data to and from the memory or the data store 408, and to generally control operations of the access point 14, 34, 36, 38 pursuant to the software instructions. In an exemplary embodiment, the processor 402 may include a mobile-optimized processor such as optimized for power consumption and mobile applications.

The radios 404 enable wireless communication in the distributed Wi-Fi system 10 or another Wi-Fi network. The radios 404 can operate according to the IEEE 802.11 standard. The radios 404 include address, control, and/or data connections to enable appropriate communications on a Wi-Fi network. As described herein, the access point 14, 34, 36, 38 includes a plurality of radios to support different links, i.e., backhaul links and client links. In an embodiment, the access points 14, 34, 36, 38 support dual-band operation simultaneously operating 2.4 GHz and 5 GHz 2×2 MIMO 802.11b/g/n/ac radios having operating bandwidths of 20/40 MHz for 2.4 GHz and 20/40/80 MHz for 5 GHz. For example, the access points 14, 34, 36, 38 can support IEEE 802.11AC1200 gigabit Wi-Fi (300+867 Mbps). The access points 14, 34, 36, 38 can also support IEEE 802.11ax (Wi-Fi 6). Of course, the access points 14, 34, 36, 38 can support future Wi-Fi standards as well.

The local interface 406 is configured for local communication to the access point 14, 34, 36, 38 and can be either a wired connection or wireless connection such as Bluetooth or the like. Since the access points 14, 34, 36, 38 are configured via the cloud 12, an onboarding process is required to first establish connectivity for a newly turned on access point 14. In an exemplary embodiment, the access points 14, 34, 36, 38 can also include the local interface 106 allowing connectivity to the user device 22 (or a Wi-Fi client device 16) for onboarding to the distributed Wi-Fi system 10 such as through an app on the user device 22. The data store 408 is used to store data. The data store 408 may include any of volatile memory elements (e.g., random access memory (RAM, such as DRAM, SRAM, SDRAM, and the like)), nonvolatile memory elements (e.g., ROM, hard drive, tape, CDROM, and the like), and combinations thereof. Moreover, the data store 408 may incorporate electronic, magnetic, optical, and/or other types of storage media.

The network interface 410 provides wired connectivity to the access point 14, 34, 36, 38. The network interface 404 may be used to enable the access point 14, 34, 36, 38 communicate to the modem/router 18. Also, the network interface 404 can be used to provide local connectivity to a Wi-Fi client device 16 or user device 22. For example, wiring in a device to an access point 14, 34, 36, 38 can provide network access to a device which does not support Wi-Fi. In an embodiment, all of the access points 14, 34, 36, 38 in the distributed Wi-Fi system 10 include the network interface 410. In another embodiment, select access points 14, 34, 36, 38 which connect to the modem/router 18 or require local wired connections have the network interface 110. The network interface 410 may include, for example, an Ethernet card or adapter (e.g., 10BaseT, Fast Ethernet, Gigabit Ethernet, 10 GbE). The network interface 410 may include address, control, and/or data connections to enable appropriate communications on the network.

The processor 402 and the data store 408 can include software and/or firmware which essentially controls the operation of the access point 14, 34, 36, 38, data gathering and measurement control, data management, memory management, and communication and control interfaces with the server 20 via the cloud. The processor 402 and the data store 408 may be configured to implement the various processes, algorithms, methods, techniques, etc. described herein.

Processes

Figure 7:
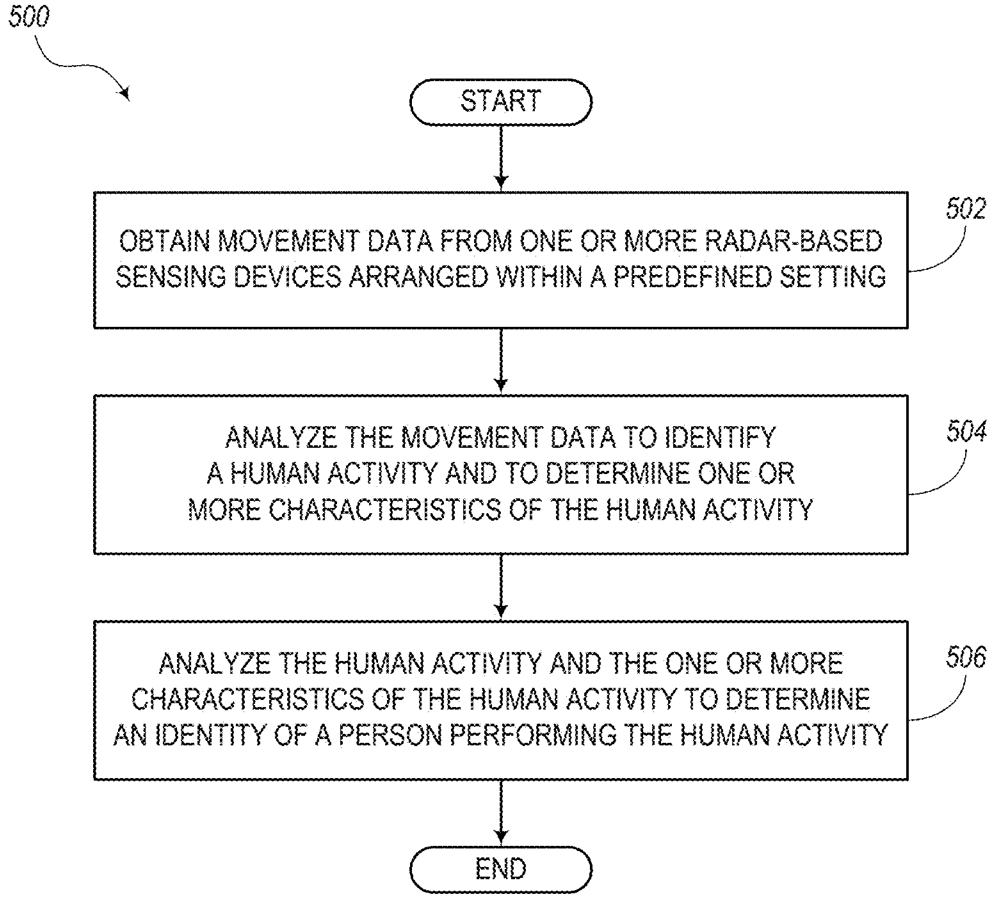
FIG. 7 is a flow diagram illustrating a process for utilizing information obtained from radar-based sensors to detect human movement within a domestic setting, according to various embodiments.

FIG. 7 is a flow diagram illustrating an embodiment of a process 500 for utilizing information obtained from radar-based sensors to detect human movement within a domestic setting. In the illustrated embodiment, the process 500 includes a step of obtaining movement data from one or more radar-based sensing devices arranged within a predefined setting, as indicated in block 502 The process 500 also include a step of analyzing the movement data to identify a human activity and to determine one or more characteristics of the human activity, as indicated in block 504. Also, the process 500 includes analyzing the human activity and the one or more characteristics of the human activity to determine an identity of a person performing the human activity, as indicated in block 506.

According to some embodiments, the process 500 may be executed by the hub device 200, access point 106, sensor 300, or other suitable device having access to the information obtained by one or more various radar detecting sensors in a monitoring system. In some embodiments, each of the one or more radar-based sensing devices may be housed in an access point (e.g., access point 106) of a local Wi-Fi network (e.g., local Wi-Fi network 100).

The movement data described above may include micro-Doppler data based on reflection signals received by the one or more radar-based sensing devices with respect to time. The one or more radar-based sensing devices may be configured to utilize one or more of Intermediate Frequency (IF) signals, Frequency Modulation (FM) signals, Continuous Wave (CW) signals, Frequency Modulation Continuous Wave (FMCW) signals, Ultra-Wideband (UWB) signals, in-phase signals, quadrature signals, pulsed reflection signals, pulsed Doppler signals, micro-Doppler signals, distance-indicating signals, and time-series signals.

The predefined setting described in block 502 may be a domestic environment having a plurality of spaces or rooms. The system may include a plurality of radar-based sensing devices oriented at one or more angles and configured to monitor one or more of the spaces or rooms of the domestic environment. For example, in some embodiments, two radar-based sensing devices may be oriented orthogonal to each other (or at any suitable angle with respect to each other) to enable the detection of movement in any direction.

The human activity may be identified out of a plurality of detectable actions including walking, running, falling, rising from a seated or lying position, lowering into a seated or lying position, exercising, carrying objects, cooking, cleaning, using a home appliance, using a computer or mobile device, opening or closing a door, moving in a wheelchair or scooter, walking with the assistance of a walker or cane, and/or any other suitable actions. The characteristics of the human activity may be identified from a list of detectable parameters including speed, acceleration, direction, location within the predefined setting, gait, balance, steadiness, variability, physical well-being, behavioral well-being, and/or other suitable detectable parameters.

The process 500 may also include the steps of characterizing the human activity in a spectrogram and utilizing the spectrogram to determine the one or more characteristics of the human activity. Determining the identity of the person performing the human activity may include distinguishing the identity of the person from one or more other people in the predefined setting. In some embodiments, identify people may further include identifying pets (e.g., dogs, cats, birds, etc.) living in the domicile and monitor the various characteristics of their movements as well. Distinguishing the identity of a specific person from the one or more other people (and pets) may include clustering the movement data based at least on location information to identify a plurality of people in the predefined setting.

The step of determining the identity of the person performing the human activity (e.g., block 506) may include comparing the one or more characteristics of the human activity with pre-stored behavioral patterns. For example, the pre-stored behavioral patterns may be based on a) supervised training data obtained by monitoring the person and used for training a Machine Learning (ML) model and/or b) generalized data representing normal human behavior obtained by monitoring a test subject in a lab.

According to some embodiments, the process 500 may also include an assessment of the behavior patterns to determine if the person is at risk of falling. For example, medical research has shown that people who tend to pause a long time after standing up before they start walking have more of a fall risk than others. Thus, the process 500 may include determining an amount of time between the action of standing up and the starting of the walking movement. This information can be used to assess fall risk. Also, the systems and methods of the present disclosure may also determine variability of steps, which may also be used to assess fall risk. Other characteristics and/or changes in behavior can be used to indicate a change (or increase) in fall risk.

In some embodiments, the process 500 may further include the step of obtaining audio data from the predefined setting when the movement data is obtained. Then, the process 500 may include combining the audio data with the movement data to enhance the identifying of the human activity and the detection of the one or more characteristics of the human activity. Also, the process 500 may include comparing the one or more characteristics of the human activity with pre-stored normal human behavior or with historic data associated with the identified person. Then, the process 500 may include determining a health or safety risk based on the comparison and automatically notifying a caregiver if the health or safety risk is greater than a predetermined threshold.

In addition, the process 500 may be further defined whereby analyzing the movement data to identify the human activity (e.g., block 502) may include identifying non-human motion data and filtering out the non-human motion data from the movement data. Identifying the non-human motion data may include identifying actions performed by a pet, a robot vacuum device (e.g., Roomba), a door, a drawer, a fan, a home appliance, and/or other spurious or background sound, noise signals, etc. In some embodiments, the process 500 may also include automatically performing any number of responsive actions, as needed. These may be based on the identification of the human activity, the one or more characteristics of the human activity, and/or the identity of the person performing the human activity. The responsive actions, for example, may include a) controlling lights, b) controlling an HVAC system, c) controlling a security system, d) controlling utility appliances, e) controlling kitchen appliances, f) controlling entertainment devices, and/or g) sending an alert or alarm signal to a family member, medical/emergency professional, or other assigned contact person.

The alerts may be further characterized based on certain activities identified. For example, in response to the detection of a fall or a fall risk assessment, an alert may be sent to medical or emergency personnel. In response to a child arriving home, an alert may be sent to a parent. In response to detection of an unidentified person (or a specifically-identified but unwelcome person) entering the home, an alert can be sent to law enforcement personnel or a trusted friend or family member. In response to detection of a seizure event, an evaluated degradation of wellness, a higher than usual fall risk, a significant reduction in walking speed, or other specifically recognizable physical or medical condition, the system may send an alert to a doctor, a doctor's office, emergency personnel, medical personnel, etc.

The responsive actions may be part of or constitute functionality of a smart home system. Therefore, as a result of radar detection as an indication of human activity, certain home automation controls may be executed. Automatic control profiles may be set up to control devices within the smart home. These profiles may be universal (i.e., for any person in the home) or individual (i.e., for each particular person). The individual controls can be programmed into the system to indicate that person's preferences or tastes. One universal control configuration may be a responsive action of turning on the lights in specific rooms when radar sensors show motion in that room. Individual controls may include the responsive actions of playing a particular type of music for a particular person, setting the lights to preferred level, color, etc. for the particular person, setting the temperature (thermostat) of an HVAC system to particular temperature for the particular person, automatically brewing a certain type of coffee for the particular person.

Also, responsive actions may include detecting certain activities and responding accordingly. For example, the systems and methods of the present disclosure (e.g., smart home system) may include, in response to detecting when a person is sleeping, performing the actions of turning off the lights, computer, television, etc., turning on a security system in all rooms except the room where person is sleeping. In response to detecting when a person leaves a home, the system may automatically turn on the security system. In response to detecting when a person wakes up and/or gets out of bed, the system may automatically turn on the lights, turn off the security system, adjust the HVAC settings, etc. In response to detecting a person doing exercises (e.g., running on a treadmill), the system may turn down the heat.

Before monitoring the movement data, the process 500 may further include the step of performing pre-processing actions on the movement data. For example, the pre-processing actions may include a) normalization, b) clipping, c) band pass filtering, d) DC offset removal, e) noise reduction, and/or other pre-processing steps. Also, other pre-processing actions may include grouping samples of the movement data to balance resolution in the time and frequency domains. For example, balancing time and frequency domains may include a process of selecting window size (for the data) that optimizes frequency resolution while maintaining sufficient time resolution to detect motion. This may include a zero padding process to increase frequency resolution while preserving responsiveness to changes in the signal. This may also include centering of the signal within the window.

In some embodiments, the process 500 may also include monitoring an identity and location of a wireless device (e.g., tracker tag 400) associated with the person to enhance determining the identity of the person performing the human activity. This wireless device may be a mobile phone, a wearable electronic device, a device for monitoring vital statistics (e.g., heart rate, etc.), an Ultra-Wideband (UWB) tracker tag, or other suitable devices.

Figure 8:
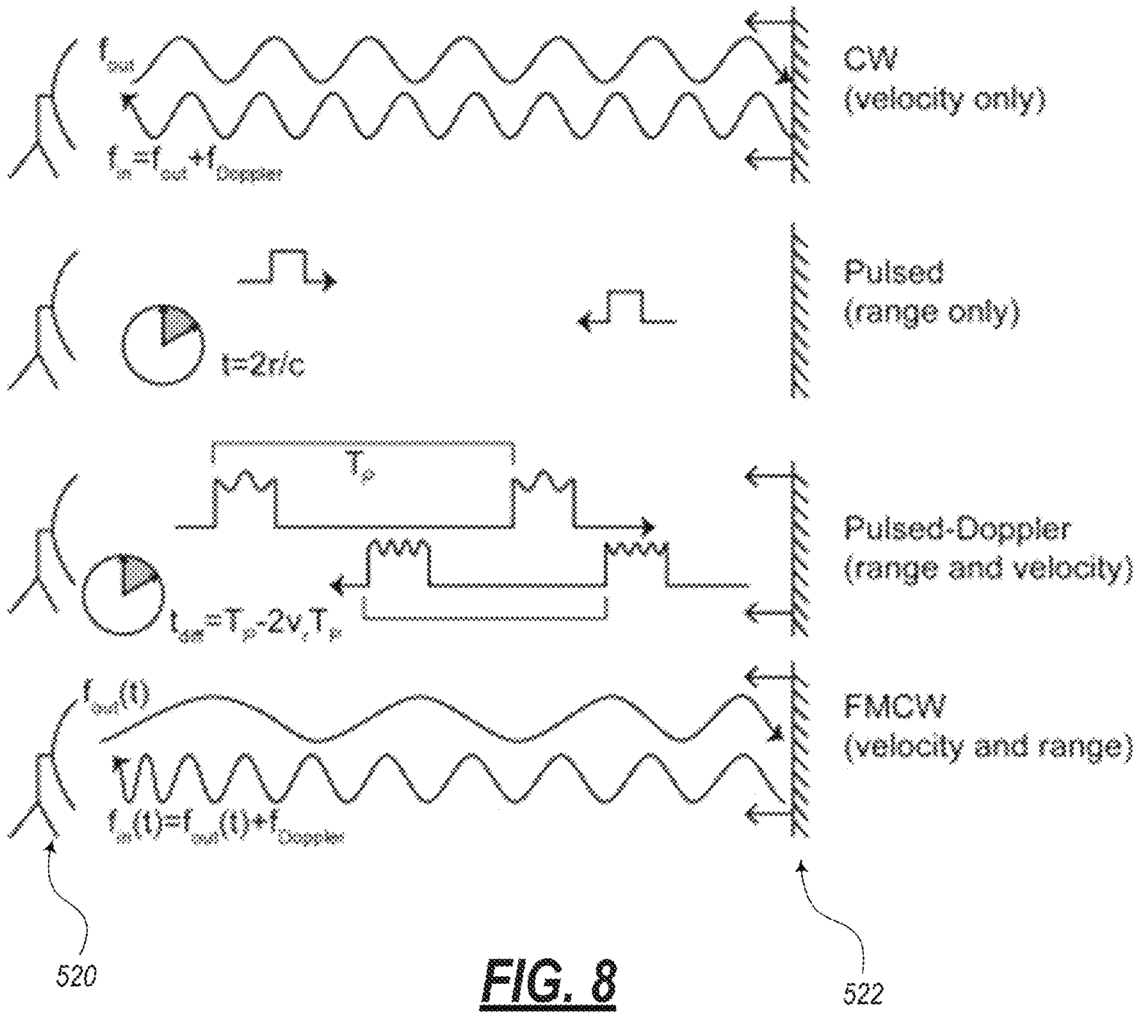
FIG. 8 is a diagram illustrating diverse types of radar transmission and reception signals used by the radar-based sensors of the local Wi-Fi network of FIG. 3, according to various embodiments.

FIG. 8 is a diagram illustrating diverse types of radar transmission and reception signals used by the radar-based sensors (e.g., sensor 300) of the local Wi-Fi network 100 of FIG. 3. The first arrangement is a Continuous Wave (CW) arrangement for detecting velocity only. The output frequency (four) radar signals are transmitted from an antenna 520 and reflect off a moving object 522 (e.g., the body of a person). The reflected signals are then received back at an antenna, which may be the same as or different from the transmitting antenna 520. For simplicity, the return antenna is shown as the same antenna 520. The input frequency (fin) reflected radar signals are equal to $f_{out}+f_{Doppler}$. These frequencies can be subtracted to obtain $f_{Doppler}$, which may be processed to determine the instantaneous velocity of the moving object 522. Also, over a period of time, these velocity values may be used to determine acceleration and deceleration.

Also, a single pulsed radar signal may be transmitted by the antenna 520, reflected off the moving object 522, and returned back to the antenna 520. The time it takes for the pulse for the pulse to make the round trip is equal to 2r/c, where r is the distance between the antenna 520 and the moving object 522 and c is the speed of light. Thus, knowing the distance between the antenna 520 and the moving object 522 can assist with the detection of the location of the moving object 522, particularly if a second sensor (with pulsed radar transmission) is used, wherein a triangulation process may be used to detect a location within a room and a direction of travel (when calculated over a period of time).

The next arrangement of FIG. 8 shows a pulsed-Doppler reflection scheme. In this case, a transmitted signal includes a periodicity $T_p$ and a predetermined frequency signature over a portion of the period. The signal reflects off the moving object 522 and returns back to the antenna 520. The return signal may be used to detect range (distance) and velocity using the formula $t_{diff}=T_p-2V_t*T_p$.

In another arrangement (shown at the bottom of FIG. 8), a Frequency Modulation Continuous Wave (FMCW) signal is used for detection of both velocity and range (distance). In this case, the output frequency is $f_{out}(t)$ and the reflected input frequency is $f_{in}(t)=f_{out}(t)+f_{Doppler}(t)$.

Figure 9:
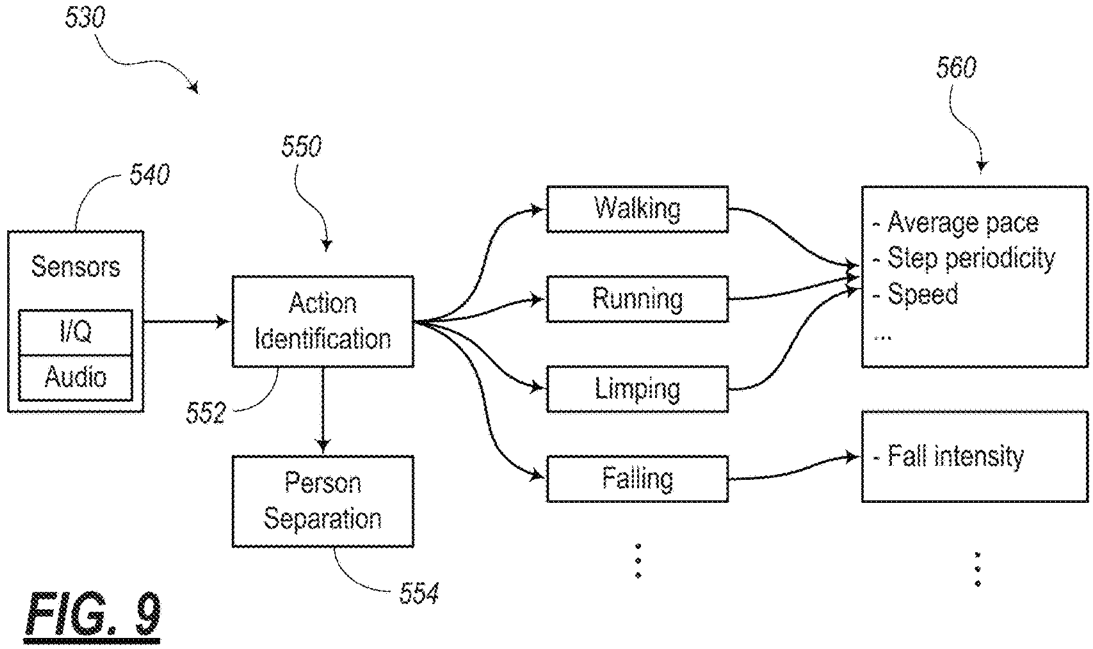
FIG. 9 is a block diagram illustrating functions of the local Wi-Fi network of FIG. 3, according to various embodiments.

FIG. 9 is an example block diagram illustrating functions of a system 530 for detecting human activity, which may be associated with the local Wi-Fi network 100 of FIG. 3 according to some embodiments. A plurality of sensors 540 may be arranged in a specific setting or environment (e.g., inside a smart home). In some embodiments, the sensors 540 may be incorporated in one or more access points of the local Wi-Fi network 100 or may be arranged external to the access points and configured to communicate sensor signals to a centralized controller (e.g., hub device 200) directly or via the one or more access points 106. The sensors 540 may include in-phase and quadrature (I/O) signal detection or other type of phase-related signal detection, which may be associated with the radar signal detection (e.g., as described with respect to FIG. 8). In some embodiments, the sensors 540 may also include other types of sensing devices, such as audio sensing devices (e.g., microphones) for obtaining audio signals.

As shown in FIG. 9, the sensor signals may be communicated to a deep learning phase 550 of the system 530 for detecting human activity. The deep learning phase 550 includes an action identification unit 552, which is configured to utilize the raw sensor data to identify one or more human activities. From these one or more human activities, the deep learning phase 550 may be configured to cluster data related to each particular human activity to separate one human activity from another.

Then, a person separation unit 554 may be used to identify which human activity is associated with each person being monitored. This operation may include a Machine Learning (ML) supervisory training process where one or more people to be monitored can be instructed to perform some standard human activities (e.g., walking, running, sitting, standing, etc.) and the detection system can detect what the reflected radar data shows. Then, this data can be used as a template for comparison when similar human activities occur in real time (i.e., after training and during use of the system). In other embodiments, an unsupervised training process may include obtaining current data and comparing the data with previously stored data. In still other embodiments, the system may be configured to store pre-fabricated standard human activities, which may be observed in a controlled environment (e.g., a lab). Then, currently obtained data can be compared with this standard data to see if anything appears to be out of the ordinary.

As shown in FIG. 9, some human activities may include "walking," "limping," "falling," "running," etc. The system 530 may further include a feature extraction phase 560, which may include classic ML techniques. The identified human activities may be compared at this phase with a normalized dataset. The feature extraction phase 560 may include the detection of an average pace, step periodicity, speed, or other characteristics of the human activities or movements. Also, if a human activity or movement is interpreted as a fall, the feature extraction phase 560 may further be able to detect specific qualities or characteristics of the fall, such as the harshness or intensity of the fall.

Figure 10:
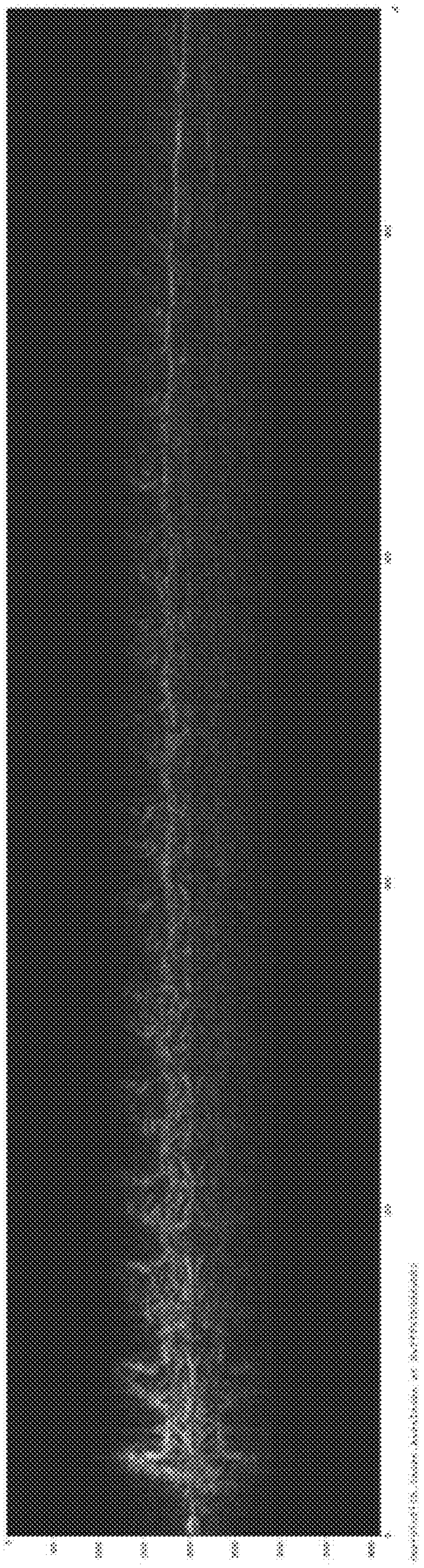
FIG. 10 is a screen shot illustrating an example of a spectrogram that shows results of radar-based detection, according to various embodiments.

FIG. 10 is a screen shot of a monitoring device showing an example of a spectrogram 570. In this embodiment, the spectrogram 570 may show the results of radar-based detection over time. For instance, the brightness of the samples may signify intensity (or energy), the y-axis may represent frequency (or velocity), and the x-axis may represent time. During the time period shown in the spectrogram 570, the processing systems of the present disclosure may be configured to analyze the detected radar signals to identify a human action, movement, or behavior. For example, the action may be interpreted as a person walking. The periodicity of the signals can be analyzed to determine certain characteristics of the walking action, such as velocity, acceleration, steadiness of the walking (based on the evenness, consistency, or inconsistency of the signal patterns over time), etc.

Figure 11:
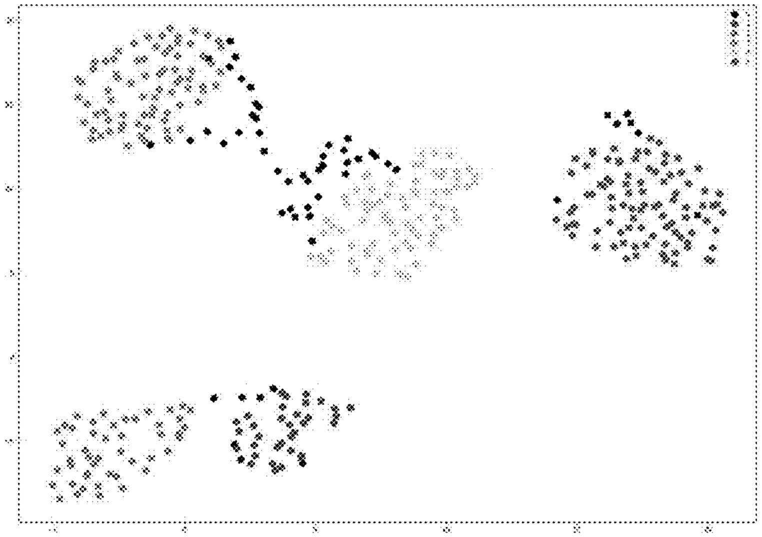
FIGS. 11-13 are spatial graphs showing examples of locations of multiple people in a space for distinguishing one person from another, according to various embodiments.
Figure 12:
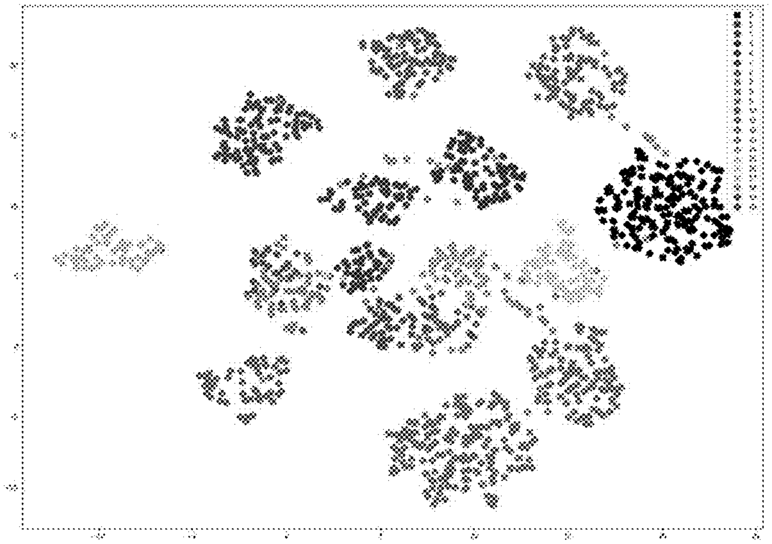
Figure 13:
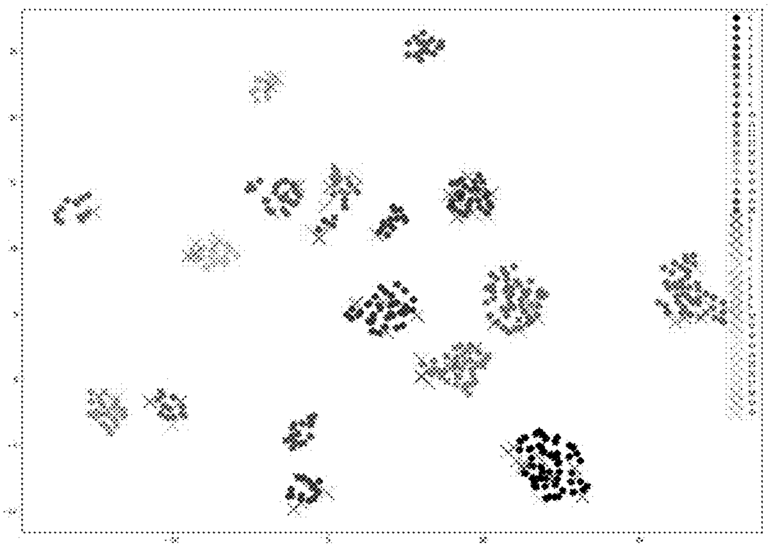

FIGS. 11-13 are spatial graphs showing examples of locations of groups or clusters of data representing multiple people in a space. This data can be used for distinguishing one person from another. In some embodiments, the processes may include a semi-supervised ML technique, which may use a contrast of currently obtained data with previously stored samples. Also, the systems and methods of the present disclosure may be configured to identify certain distinct people and eliminate those people who are not meant to be monitored. For example, user input may be provided which instructs the present systems and methods to only monitor one person, whose identity is determined from the data samples. Other embodiments may include monitoring the normal residents of a home, monitoring one or more caregivers, monitoring one or more regular guests, monitoring regularly-scheduled nurses, physical therapists, occupational therapists, monitoring other family members, monitoring house cleaners and other regular service personnel, and/or monitoring other people who may regularly be present in the home. Validation may include leaving one or more people out and/or a stratified split per person.

Figure 14:
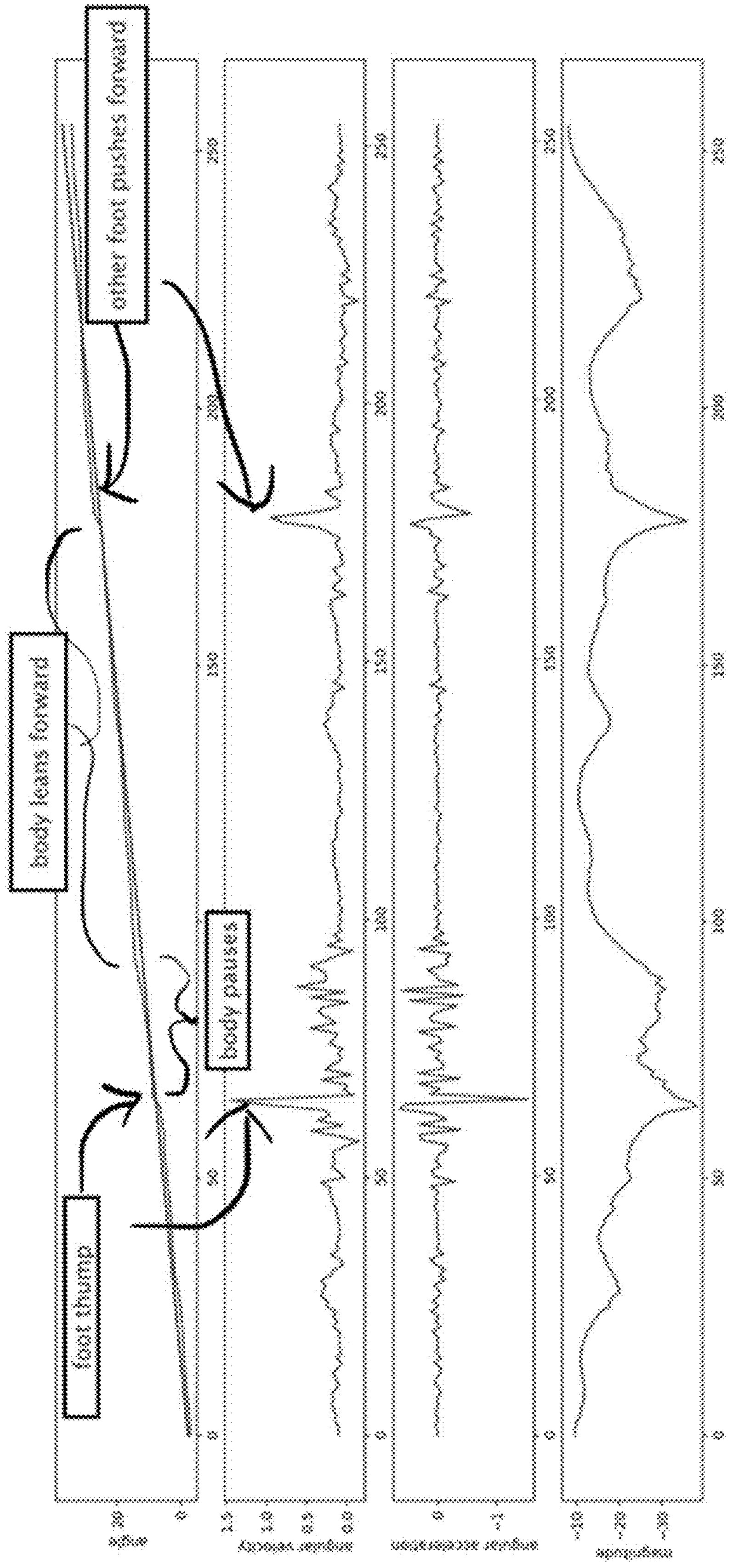
FIG. 14 is a graph showing an example of characteristics of a walking activity, according to various embodiments.

FIG. 14 is a graph 600 showing an example of characteristics of a walking activity. The graph 600 shows an example where the human activity of "walking" has been identified and then further processing has been performed to obtain certain parameters of the walking activity. In this example, the hub device 200 (or other device configured to obtain radar-based sensor data of human movement from one or more sensors) is configured to receive the movement data and perform various processing steps on the data. For example, as shown in the graph 600, phase angle, angular velocity, angular acceleration, and magnitude may be measured. From this data, certain characteristics of the walking activity can be detected. Particularly, the hub device 200 may be configured to determine, from the information shown in FIG. 14, when a foot thumps on the floor and the intensity of this thump, when a body pauses, when a body leans forward, when another foot moves forward and thumps on the floor, etc.

Figure 15:
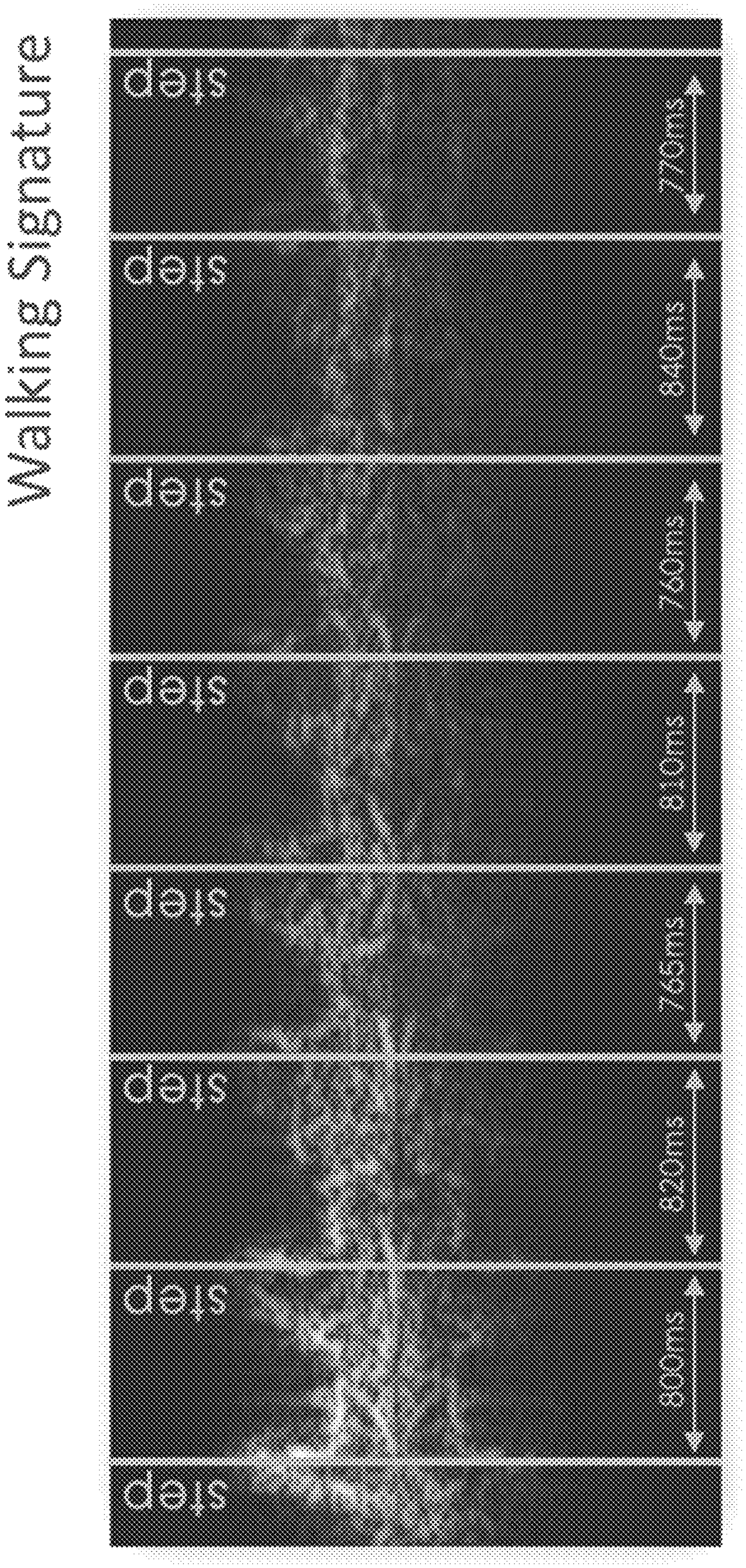
FIG. 15 is a screen shot illustrating an example of a spectrogram that shows a walking signature, according to various embodiments.

FIG. 15 is a screen shot illustrating an example of a spectrogram 610 that shows a walking signature. The spectrogram 610 may be used the processing systems of the present disclosure to detect certain features of the walking signature. In this example, a number of steps can be detected and the time between each step can be calculated. According to this example, every odd step has a general timing that is different from every even step. This may be an indication of a limp, for instance. Also, the information gained from the spectrogram 610 may be used to determine the speed of the person walking, the direction of movement, any variability in the steps, etc.

In some embodiments, the processing of the spectrogram 610 may include identifying that the samples show a walking signature. Then, the processing may include figuring out which portion of the spectrogram 610 represent a first step, which may be based on energy accumulated. The first step information can be used to make a template that can be compared with a second step, which may be identified by shifting the first step template forward in time and comparing the second step with the first. This process can be repeated to find any inconsistencies in the walking pattern.

By converting human activity information to the form of the spectrogram 610, it may be possible to determine characteristics of the human activity. The spectrogram 610 may include spectrum (with amplitude and phase) with respect to time to show how characteristics of the human activity change over time. In some cases, a two-dimensional median filtering may be applied to the spectrogram 610 to remove noise and extraneous frequencies.

In some embodiments, the hub device 200 may be configured to use ML procedures (algorithms) on the spectrograms to do action identification. For example, a closed set of only a certain number or type of actions may be considered. In this case, processing the spectrogram 610 may include a classification process, where the classification includes identifying the human activity (e.g., walking, running, sleeping, falling, stumbling, etc.). The classification may also include gait detection. A ML model can be trained on one set of people (e.g., in the lab), which may be generalized for use in any home for identifying the same or similar activities for different customers.

Therefore, according to various embodiments of the present disclosure, systems and methods may be provided for obtaining and utilizing information from one or more radar-based sensors to detect human movement within a domestic setting or other predefined setting. The present embodiments may include analyzing the movement data to identify a human activity and to determine one or more characteristics of the human activity. Then, the systems and methods of the present disclosure are configured to analyze the human activity and the one or more characteristics of the human activity to determine an identity of a person performing the human activity.

This movement data may be micro-Doppler data or other suitable reflection signals received by the one or more radar-based sensing devices with respect to time. Multiple sensors may be arranged in a common space, whereby the sensors may have monitoring fields of view with a predetermined angle between them. For example, two sensors in a room may be directed (from a sensing point of view) substantially orthogonal to each other or at any other suitable angle to enable better sensor coverage and to allow one sensor to pick up movement in one direction (e.g., toward or away from the sensor) while this movement may be side-to-side with respect to the other sensor. A pair radar-based sensing devices may be oriented orthogonal to each other (or at any suitable angle with respect to each other) to thereby enable the detection of movement in any direction.

The one or more radar-based sensing devices may be configured to utilize Intermediate Frequency (IF) signals, Frequency Modulation (FM) signals, Continuous Wave (CW) signals, Frequency Modulation Continuous Wave (FMCW) signals, Ultra-Wideband (UWB) signals, in-phase signals, quadrature signals, pulsed reflection signals, pulsed Doppler signals, micro-Doppler signals, distance-indicating signals, time-series signals, etc. As mentioned with respect to FIG. 8, some radar technology may allow the detection of velocity, while others may allow range (distance). Still others may allow both velocity detection and range detection. Any suitable radar signal transmission, reception, and subsequent processing may be used for detecting several types of human activities.

The human activity may be identified out of a plurality of detectable actions, based on the particular processing capabilities and machine learning technology utilized by the hub device 200 or other data processing system. The detectable actions, for example, may include walking, jogging, running, running on a treadmill, exercising, falling down, gently or not-so-gently rising from a seated or lying position, gently or not-so-gently lowering into a seated or lying position, carrying bags of groceries, cooking, cleaning, using a home appliance, using a computer or mobile device, opening or closing a door (e.g., refrigerator door), moving in a wheelchair or scooter, walking with the assistance of a walker or cane, and/or any other types of actions that may be identified using any suitable technology.

The characteristics of these human activity may then be further processed (e.g., by the hub device 200) and identified from a list of detectable characteristics or parameters. For example, some of these parameters may include speed of movement (e.g., speed of walking), acceleration, direction of movement, particular location within the predefined setting, gait (e.g., rhythm of movement), balance, evenness, steadiness, variability, limp, etc. In some embodiments, the hub device 200 may be configured to analyze the information about the human activity to detect certain movement characteristics that may lead to an understanding of physical well-being (e.g., whether or not an identified person is walking more slowly or more erratically), behavioral well-being (e.g., whether or not an identified person is spending more time on the computer or watching television), etc. Thus, the hub device 200 may further detect a change in behavior to determine, for example, if a person is limping more, walking slower, etc. Comparisons of the detailed analysis factors can be made by looking at the difference in behavior from day to day or according to certain routines throughout a day, week, month, season, year, etc. This type of information can also be used to assess wellness to determine if someone might be sick. Also, analyzing over time may reveal whether a person's condition is degrading.

In some embodiments, the hub device 200 (or other centralized processing system) may be configured to characterize the human activity in a spectrogram. By converting this information into a spectrogram, the hub device 200 maybe configured to determine the one or more characteristics of the human activity mentioned above. The spectrogram may include spectrum (with amplitude and phase) with respect to time to show how characteristics of the human activity change over time. In some cases, the hub device 200 may apply two-dimensional median filtering to removes noise and extraneous frequencies.

Determining the identity of the person performing the various human activities may include distinguishing the identity of the person from one or more other people (and/or pets) in the predefined setting. For example, distinguishing the identity of the person from the one or more other people (and/or pets) may include a clustering process for grouping the movement data based at least on location information to identify a plurality of people in the predefined setting. This grouping step may involve the use of information from the tracker tags 108 in some cases.

The step of determining the identity of the person performing the human activity may also include comparing the one or more characteristics of the human activity with pre-stored behavioral patterns. For example, the pre-stored behavioral patterns may be based on supervised training data obtained by monitoring the person and used for training a Machine Learning (ML) model. Supervised training may include performing functions (e.g., via an app) to instruct a person to walk back and forth in front of the sensors to allow the sensors to record the movement information. This can be repeated for different activities (e.g., walking, running, getting up from a chair, opening a refrigerator door, etc.). The app may then instruct the user to identify who was present at each time that the actions were monitored in order to label the data with human identity information.

Also, the pre-stored behavior patterns may be based on unsupervised training data. This may include generalized data representing normal human behavior obtained by monitoring a test subject in a lab. For example, unsupervised training may include clustering human activity data into groups to identify individual people. The app may include receiving verification or input from user about the number of different people in the space when the human activity was monitored. This too might be repeated for each of a number of different activities identified (e.g., walking, cooking, using the computer, sleeping, etc.). In some embodiments, unsupervised training may include using Wi-Fi information (e.g., host name of a phone, MAC address of a phone, etc.) to identify a person and their location in the home at various times and using this information to label the clusters with names. Also, the tracker tag 400 (e.g., UWB tag) may be configured to provide ID information of specific users.

In some embodiments, audio data may be obtained (e.g., from microphones in the sensors, access points, or elsewhere) from the predefined setting, which can be obtained at the same time the movement data is obtained. The hub device 200 may utilize this audio data along with the movement data, in combination, to enhance the step of identifying of the human activity and to enhance the step of detecting the one or more characteristics of the human activity. The audio data may be used to "cross check" the radar data. Audio information may be used when a fall identification is identified to cross check whether the audio information may indicate something different than what may have been determined with the radar information alone. For example, if the audio information detects the sound of people laughing, then it may be determined that the fall event was not an event that requires medical attention. Otherwise, if the audio information detects the sound of a person calling for help, then it can be determined that the event was indeed something that might require medical attention.

The hub device 200 may also compare the one or more characteristics of the human activity with pre-stored normal human behavior or with historic data associated with the identified person. Then, the hub device 200 can determine a health or safety risk based on the comparison and may also automatically notify a caregiver, emergency personnel, medical personnel, family member, or other trusted or assigned person if the health or safety risk is greater than a predetermined threshold.

In addition, the processing of the human activity data may also include identifying non-human motion data and then filtering out this non-human motion data from the movement data that actually represents human motion. For example, some non-human motion data may be the result of identifying actions that might be performed by a pet, a robot vacuum device (e.g., Roomba), a door (e.g., regular room door, refrigerator door, microwave door, etc.), a drawer (e.g., kitchen drawer, dresser drawer, etc.), a fan (e.g., ceiling fan, oscillating fan, etc.), a home appliance (e.g., washer, dryer, etc.), etc. These non-human motion data may be considered to naturally provide spurious or background sound, noise signals, etc. that can be detected for better identifying the non-human actions.

In some embodiments, any number of responsive actions may be performed as a result of the detection and analysis of the human activities and quality of the activities. These may be based on the identification of the human activity, the one or more parameters/characteristics of the human activity, and/or the identity of the person performing the human activity. In some respects, identifying the quality of an activity may even include, for example, determining sleep time and sleep quality. The responsive actions, for example, may include a) controlling lights, b) controlling an HVAC system, c) controlling a security system, d) controlling utility appliances, e) controlling kitchen appliances, f) controlling entertainment devices, g) sending an alert to family members and/or medical/emergency professionals, and/or other types of responsive actions.

Before monitoring the movement data, the activity information processing device (e.g., hub device 200) may be configured to perform certain pre-processing actions on the movement data. For example, the pre-processing actions may include a) normalization, b) clipping, c) band pass filtering, d) DC offset removal, e) noise reduction, and/or other pre-processing steps. Also, other pre-processing actions may include grouping samples of the movement data to balance resolution in both the time domain and frequency domain. In some embodiments, the hub device 200 may monitor an identity and location of a wireless device (e.g., tracker tag 400) associated with a particular person to enhance the human identification procedure. Besides the tracker tag 400, other wireless devices (e.g., mobile phones or other wearable or portable electronic devices) may be used for this purpose.

Conclusion

It will be appreciated that some embodiments described herein may include one or more generic or specialized processors ("one or more processors") such as microprocessors; Central Processing Units (CPUs); Digital Signal Processors (DSPs): customized processors such as Network Processors (NPs) or Network Processing Units (NPUs), Graphics Processing Units (GPUs), or the like; Field Programmable Gate Arrays (FPGAs); and the like along with unique stored program instructions (including both software and firmware) for control thereof to implement, in conjunction with certain non-processor circuits, some, most, or all of the functions of the methods and/or systems described herein. Alternatively, some or all functions may be implemented by a state machine that has no stored program instructions, or in one or more Application-Specific Integrated Circuits (ASICs), in which each function or some combinations of certain of the functions are implemented as custom logic or circuitry. Of course, a combination of the aforementioned approaches may be used. For some of the embodiments described herein, a corresponding device in hardware and optionally with software, firmware, and a combination thereof can be referred to as "circuitry configured or adapted to," "logic configured or adapted to," etc. perform a set of operations, steps, methods, processes, algorithms, functions, techniques, etc. on digital and/or analog signals as described herein for the various embodiments.

Moreover, some embodiments may include a non-transitory computer-readable storage medium having computer readable code stored thereon for programming a computer, server, appliance, device, processor, circuit, etc. each of which may include a processor to perform functions as described and claimed herein. Examples of such computer-readable storage mediums include, but are not limited to, a hard disk, an optical storage device, a magnetic storage device, a ROM (Read Only Memory), a PROM (Programmable Read Only Memory), an EPROM (Erasable Programmable Read Only Memory), an EEPROM (Electrically Erasable Programmable Read Only Memory), Flash memory, and the like. When stored in the non-transitory computer-readable medium, software can include instructions executable by a processor or device (e.g., any type of programmable circuitry or logic) that, in response to such execution, cause a processor or the device to perform a set of operations, steps, methods, processes, algorithms, functions, techniques, etc. as described herein for the various embodiments.

Although the present disclosure has been illustrated and described herein with reference to preferred embodiments and specific examples thereof, it will be readily apparent to those of ordinary skill in the art that other embodiments and examples may perform similar functions and/or achieve like results. All such equivalent embodiments and examples are within the spirit and scope of the present disclosure, are contemplated thereby, and are intended to be covered by the following claims.

What is claimed is:

1. A system comprising:

a processing device; and a memory device configured to store instructions that, when executed, enable the processing device to:

obtain movement data from at least one of a plurality of radar-based sensing devices arranged within a predefined setting;

analyze the movement data;

identify, based on the analysis of the movement data, a human activity;

further analyzing the movement data based on the identified human activity, the further analysis comprising identifying non-human motion data and filtering out the non-human motion data from the movement data;

determine, based on the further analysis of the movement data, one or more characteristics of the human activity, the one or more characteristics corresponding to a type of behavior that is indicative of a risk associated with the human activity;

analyze the one or more characteristics of the human activity; and determine an identity of a person performing the human activity by:

(i) distinguishing among two or more individuals concurrently present in the predefined setting by clustering the movement data based at least on location information to identify a plurality of people in the predefined setting and (ii) comparing the one or more characteristics of the human activity with pre-stored per-person behavioral templates over a historical time window to differentiate the person from one or more other people.

2. The system of claim 1, wherein at least one of the plurality of radar-based sensing devices are housed in an access point of a local Wi-Fi network.

3. A method comprising:

obtaining movement data from one or more radar-based sensing devices arranged within a predefined setting;

analyzing the movement data;

identify, based on the analysis of the movement data, a human activity;

further analyze the movement data based on the identified human activity, the further analysis comprising identifying non-human motion data and filtering out the non-human motion data from the movement data;

determine, based on the further analysis of the movement data, one or more characteristics of the human activity, the one or more characteristics corresponding to a type of behavior that is indicative of a risk associated with the human activity;

analyzing the one or more characteristics of the human activity; and determine an identity of a person performing the human activity by:

(i) distinguishing among two or more individuals concurrently present in the predefined setting by clustering the movement data based at least on location information to identify a plurality of people in the predefined setting and (ii) comparing the one or more characteristics of the human activity with pre-stored per-person behavioral templates over a historical time window to differentiate the person from one or more other people.

4. The method of claim 3, wherein the movement data includes micro-Doppler data based on reflection signals received by the one or more radar-based sensing devices with respect to time.

5. The method of claim 3, wherein the one or more radar-based sensing devices are configured to utilize one or more of Intermediate Frequency (IF) signals, Frequency Modulation (FM) signals, Continuous Wave (CW) signals, Frequency Modulation Continuous Wave (FMCW) signals, Ultra-Wideband (UWB) signals, in-phase signals, quadrature signals, pulsed reflection signals, pulsed Doppler signals, micro-Doppler signals, distance-indicating signals, and time-series signals.

6. The method of claim 3, wherein the predefined setting is a domestic environment having a plurality of spaces or rooms, and wherein the one or more radar-based sensing devices include a plurality of radar-based sensing devices oriented at one or more angles and configured to monitor one or more of the spaces or rooms of the domestic environment.

7. The method of claim 3, wherein the human activity is identified out of a plurality of detectable actions including one or more of walking, running, falling, rising from a seated or lying position, lowering into a seated or lying position, exercising, carrying objects, cooking, cleaning, using a home appliance, using a computer or mobile device, opening or closing a door, moving in a wheelchair or scooter, and walking with the assistance of a walker or cane.

8. The method of claim 3, wherein the one or more characteristics of the human activity are identified out of a plurality of detectable parameters including one or more of speed, acceleration, direction, location within the predefined setting, gait, balance, steadiness, variability, physical well-being, and behavioral well-being.

9. The method of claim 3, further comprising using the one or more characteristics of the human activity to determine a fall risk or a change in fall risk.

10. The method of claim 3, wherein the identified human activity is sleeping, and further comprising assessing quality of the sleeping.

11. The method of claim 3, further comprising:

characterizing the human activity in a spectrogram; and utilizing the spectrogram to determine the one or more characteristics of the human activity.

12. The method of claim 3, wherein determining the identity of the person performing the human activity includes distinguishing the identity of the person from one or more other people in the predefined setting.

13. The method of claim 12, wherein distinguishing the identity of the person from the one or more other people includes clustering the movement data to identify a plurality of people in the predefined setting.

14. The method of claim 3, wherein determining the identity of the person performing the human activity includes comparing the one or more characteristics of the human activity with pre-stored behavioral patterns.

15. The method of claim 14, wherein the pre-stored behavioral patterns are based on one or more of:

supervised training data obtained by monitoring the person and used for training a Machine Learning (ML) model, and generalized data representing human behavior obtained by monitoring a test subject in a lab.

16. The method of claim 3, wherein determining the identity of the person includes requesting via a mobile application the user to walk in front of the radar at a known time or allowing the user to enter the identity and time at which a person was walking in front of the sensor.

17. The method of claim 3, further comprising obtaining a number of people who have been present in a location.

18. The method of claim 17, wherein the one or more responsive actions includes notifying the owner, a family member, an assigned contact, a medical professional, emergency personnel.

19. The method of claim 3, further comprising:

obtaining audio data from the predefined setting when the movement data is obtained; and combining the audio data with the movement data to enhance the identifying of the human activity and the detection of the one or more characteristics of the human activity or to distinguish of the identity of the individual.

20. The method of claim 3, further comprising:

comparing the one or more characteristics of the human activity with pre-stored human behavior or with historic data associated with the identified person;

determining a health or safety risk based on the comparison; and automatically notifying a caregiver if the health or safety risk is greater than a predetermined threshold.

21. The method of claim 3, wherein identifying the non-human motion data includes identifying one or more actions performed by a pet, a robot vacuum device, a door, a drawer, a fan, and a home appliance.

22. The method of claim 21, further comprising reporting the identified non-human activity or a change in the non-human activity to the user.

23. The method of claim 21, wherein the non-human activity is identified to be associated with a specific pet.

24. The method of claim 3, further comprising automatically performing one or more responsive actions based on one or more of:

the identification of the human activity, the one or more characteristics of the human activity, and the identity of the person performing the human activity.

25. The method of claim 24, wherein the one or more responsive actions includes one or more of controlling lights, controlling an HVAC system, controlling a security system, controlling utility appliances, controlling kitchen appliances, controlling entertainment devices, and sending an alert to a family member or a medical or emergency professional.

26. The method of claim 3, wherein, before monitoring the movement data, the method further comprises performing pre-processing actions on the movement data, the pre-processing actions including one or more of normalization, clipping, band pass filtering, DC offset removal, noise reduction, and grouping samples of the movement data to balance resolution in the time and frequency domains.

27. The method of claim 3, further comprising monitoring an identity and location of a wireless device associated with the person to enhance determining the identity of the person performing the human activity, wherein the wireless device is one or more of a mobile phone, a wearable electronic device, and an Ultra-Wideband (UWB) tracker tag.

28. The method of claim 3, further comprising combining digital device usage statistics including app usage, screen time, and types of websites visited with radar data to determine a well-being of an individual that is based on a physical well-being and behavioral well-being.

29. The method of claim 3, further comprising combining statistics from a wearable device with radar data to determine a status of an individual.

* * * * *